US007943146B2

(12) United States Patent
Hobden et al.

(10) Patent No.: US 7,943,146 B2
(45) Date of Patent: May 17, 2011

(54) IMMUNIZING COMPOSITIONS COMPRISING HIV-1 PROVIRAL CONSTRUCTS WITH AN INACTIVE P6 GAG TSG101 UEV BINDING DOMAIN CAPABLE OF PRODUCING BUDDING-DEFECTIVE VIRAL PARTICLES THAT REMAIN TETHERED TO THE CELL SURFACE

(75) Inventors: Adrian Hobden, Salt Lake City, UT (US); Kenton Zavitz, Salt Lake City, UT (US); Scott Morham, Salt Lake City, UT (US)

(73) Assignee: Myrexis, Inc., Salt Lake City, UT (US)

( * ) Notice: Subject to any disclaimer, the term of this patent is extended or adjusted under 35 U.S.C. 154(b) by 1700 days.

(21) Appl. No.: 10/327,685

(22) Filed: Dec. 20, 2002

(65) Prior Publication Data

US 2011/0076248 A1    Mar. 31, 2011

Related U.S. Application Data

(60) Provisional application No. 60/342,692, filed on Dec. 21, 2001.

(51) Int. Cl.
A61K 39/21    (2006.01)
(52) U.S. Cl. ................................................... 424/208.1
(58) Field of Classification Search .............. 424/188.1, 424/208.1; 536/23.72
See application file for complete search history.

(56) References Cited

U.S. PATENT DOCUMENTS

| | | | |
|---|---|---|---|
| 5,443,828 A | 8/1995 | Kang et al. | |
| 5,807,995 A | 9/1998 | Cohen et al. | |
| 5,891,668 A | 4/1999 | Li et al. | |
| 5,892,016 A | 4/1999 | Brie et al. | |
| 5,965,726 A * | 10/1999 | Pavlakis et al. | 536/23.72 |
| 6,099,847 A | 8/2000 | Tobin et al. | |
| 6,248,523 B1 | 6/2001 | Cohen et al. | |
| 6,274,312 B1 | 8/2001 | Gish et al. | |
| 6,291,227 B1 * | 9/2001 | Haynes et al. | 435/236 |
| 6,348,449 B1 * | 2/2002 | Weiner et al. | 514/44 |

FOREIGN PATENT DOCUMENTS

| | | |
|---|---|---|
| WO | WO 02/072790 | 9/2002 |
| WO | WO 02/094314 | 11/2002 |
| WO | WO 03/015708 | 2/2003 |
| WO | WO 03/053332 | 7/2003 |

OTHER PUBLICATIONS

Garrus, J. E., et al., 2001, Tsg101 and the vacuolar protein sorting pathway are essential for HIV-1 budding, Cell 107:55-65.*
Wyma, D. J., et al., 2000, Evidence for a stable interaction of gp41 with Pr55Gag in immature human immunodeficiency virus type 1 particles, J. Virol. 74(20):9381-9387.*
2008, Instructions to authors, J. Virol. 82:1):1-19.*
Garnier, L., et al., 1998, Particle size determinants in the human immunodeficiency virus type 1 Gag protein, J. Virol. 72(6):4667-4677.*
Barouch, D. H., et al., 2000, Control of viremia and prevention of clinical AIDS in rhesus monkeys by cytokine-augmented DNA vaccination, Science 290:486-492.*
Farrar, Graham H., et al., "Characterisation of a Series of Human Immunodeficiency Virus Isolates Derived Sequentially From a Single Patient", *Journal of Medical Virology*, 1991; 34:104-113.
Schwartz, Stefan, et al., "Mutational Inactivation of an Inhibitory Sequence in Human Immunodeficiency Virus Type 1 Results in Rev-Independent *gag* Expression", *Journal of Virology*, Dec. 1992; 66(12):7176-7182.
Fynan, Ellen F., et al., "DNA vaccines: Protective immunizations by parenteral, mucosal, and gene-gun inoculations", *Proc. Natl. Acad. Sci. USA*, Dec. 1993; 90:11478-11482.
Whittle, Peter J., "Protein Structure-Based Drug Design", *Annu. Rev. Biophys. Biomol. Struct.*, 1994; 23:34-375.
Mhashilkar, Abner, et al., "Inhibition of HIV-1 Tat-mediated LTR transactivation and HIV-1 infection by anti-Tat single chain intrabodies", *The EMBO Journal*, 1995; 14(7):1542-1551.
U.S. Appl. No. 09/971,549, filed Oct. 4, 2001, Zavitz et al.
U.S. Appl. No. 09/972,035, filed Nov. 21, 2002, Wettstein et al.
U.S. Appl. No. 10/098,979, filed Nov. 28, 2002, Sugiyama et al.
U.S. Appl. No. 10/097,534, filed Mar. 13, 2003, Greener et al.
U.S. Appl. No. 10/223,172, filed Jul. 24, 2003, Zavitz et al.
U.S. Appl. No. 10/224,999, filed Sep. 11, 2003, Morham et al.
U.S. Appl. No. 10/663,407, filed Sep. 15, 2003, Zavitz et al.
Parent, Leslie J., et al., "Positionally Independent and Exchangeable Late Budding Functions of the Rous Sarcoma Virus and Human Immunodeficiency Virus Gag Proteins", *Journal of Virology*, Sep. 1995; 69(9):5455-5460.
Huang, Mingjun, et al., "$p6^{GAG}$ Is Required for Particle Production from Full-Length Human Immunodeficiency Virus Type 1 Molecular Clones Expressing Protease", *Journal of Virology*, Nov. 1995; 69(11):6810-6818.
NCBI Entrez Protein Database Accession No. AAB38034, Dec. 5, 1996.
Rossi, John J., Therapeutic applications of catalytic Antisense RNAs (ribozymes), *CIBA Foundation Symposium*, 1997; 209:195-204.
Levin, Rueven, et al., "Inhibition of Early and Late Events of the HIV-1 Replication Cycle by Cytoplasmic Fab Intrabodies against the Matrix Protein, p17", *Molecular Medicine*, Feb. 1997; 3(2):96-110.
Roman, Mark, et al., "Immunostimulatory DNA sequences function as T helper-1- promoting adjuvants", *Nature Medicine*, Aug. 1997; 3(8):849.
Burton, Dennis R., "A vaccine for HIV type 1: The antibody perspective", *Proc. Natl. Acad. Sci. USA*, Sep. 1997; 94:10018-10023.
Puffer, Bridget A., et al., "Equine Infectious Anemia Virus Utilizes a YXXL Motif within the Late Assembly Domain of the Gag p9 Protein", *Journal of Virology*, Sep. 1997; 71(9):6541-6546.

(Continued)

*Primary Examiner* — Jeffrey S Parkin
(74) *Attorney, Agent, or Firm* — Kelly A. Echols; Herbert L. Ley, III; Myrexis IP Group

(57) ABSTRACT

The present invention provides methods for preventing and treating HIV infection and AIDS by introducing cells displaying HIV late-domain phenotype into a patient, or by administering to a patient nucleic acids, polypeptides or small organic compounds to cause the formation of cells displaying HIV late-domain phenotype in the body of the patient.

OTHER PUBLICATIONS

Figure 1:
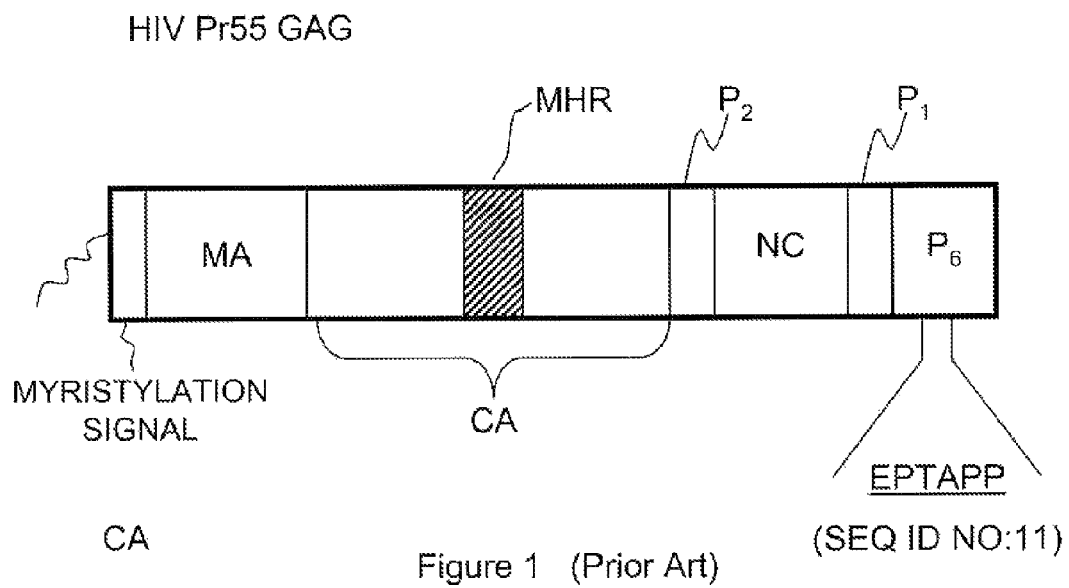

Zhang, Yi-Ming, et al., "Drug Resistance during Indinavir Therapy Is Caused by Mutations in the Protease Gene and in Its Gag Substrate Cleavage Sites, *Journal of Virology*", Sep. 1997; 71(9):6662-6670.

NCBI Entrez Protein Database Accession No. AAB83138, Nov. 6, 1997.

NCBI Entrez Protein Database Accession No. AAB83216, Nov. 6, 1997.

NCBI Entrez Protein Database Accession No. AAB83821, Nov. 6, 1997.

Savarino, Andrea, et al., "The Biochemistry of Gene Therapy for AIDS", *Clin. Chem. Lab. Med.*, 1998; 36(4):205-210.

Zhang, Yaqiang, et al., "Analysis of the Assembly Function of the Human Immunodeficiency Virus Type 1 Gag Protein Nucleocapsid Domain", *Journal of Virology*, Mar. 1998: 72(3):1782-1789.

Yasuda, Jiro, et al., "A Proline-Rich Motif (PPPY) in the Gag Polyprotein of Mason-Pfizer Monkey Virus Plays a Maturation-Independent Role in Virion Release", *Journal of Virology*, May 1998; 72(5):4095-4103.

Letvin, Norman L., "Progress in the Development of an HIV-1 Vaccine", *Science*, Jun. 19, 1998: 280:1875-1880.

NCBI Entrez Protein Database Accession No. P35962, Jul. 15, 1998.

Crump, Colin M., et al., "Inhibition of the Interaction between Tyrosine-based Motifs and the Medium Chain Subunit of the AP-2 Adaptor Complex by Specific Tyrphostins", *The Journal of Biological Chemistry*, Oct. 23, 1998; 273(43):28073-28077.

Borsetti, Alessandra, et al., "The C-Terminal Half of the Human Immunodeficiency Virus Type 1 Gag Precursor Is Sufficient for Efficient Particle Assembly", *Journal of Virology*, Nov. 1998: 72(11):9313-9317.

Dubensky, Thomas W., et al., "Live virus vaccines: Something old, something new, something borrowed . . . ", *Nature Medicine*, Dec. 1998; 4(12):1357-1358.

Puffer, Bridget A., et al., "Equine Infectious Anemia Virus Gag Polyprotein Late Domain Specifically Recruits Cellular AP-2 Adapter Protein Complexes during Virion Assembly", *Journal of Virology*, Dec. 1998; 72(12):10218-10221.

Sorkina, Tatiana, et al., "Clathrin, adaptors and eps15 in endosomes containing activated epidermal growth factor receptors", *Journal of Cell Science*, 1999: 112:317-327.

Verkhivker, Gennady M., et al., "Towards understanding the mechanisms of molecular recognition by computer simulations of ligand-protein interactions", *Journal of Molecular Recognition*, 1999; 12:371-389.

Yuan, Bing, et al., "Mutations altering the Moloney murine leukemia virus p12 Gag protein affect virion production and early events of the virus life cycle", *The EMBO Journal*, 1999; 18(17):4700-4710.

NCBI Entrez Protein Database Accession No. AAD03232, Jan. 6, 1999.

NCBI Entrez Protein Database Accession No. AAD03240, Jan. 6, 1999.

Garnier, Laurence, et al., "Identification of Retroviral Late Domains as Determinants of Particle Size", *Journal of Virology*, Mar. 1999; 73(3):2309-2320.

Craven, Rebecca C. et al., "Late Domain Function Identified in the Vesicular Stomatitis Virus M Protein by Use of Rhabdovirus-Retrovirus Chimeras", *Journal of Virology*, Apr. 1999; 73(4):3359-3365.

Harty, Ronald N., et al., "A Proline-Rich Motif within the Matrix Protein of Vesicular Stomatitis Virus and Rabies Virus Interacts with WW Domains of Cellular Proteins: Implications for Viral Budding", *Journal of Virology*, Apr. 1999; 73(4):2921-2929.

Harvey, Kieran F., et al., "Nedd4-like proteins: an emerging family of ubiquitin-protein ligases implicated in diverse cellular functions", *Trends in Cell Biology*, May 1999: 9;166-169.

Li, Yu, et al., "Yeast Mutants Affecting Possible Quality Control of Plasma Membrane Proteins", *Molecular and Cellular Biology*, May 1999; 19(5):3588-3599.

Deschambeault, Julie, et al., "Polarized Human Immunodeficiency Virus Budding in Lymphocytes Involves a Tyrosine-Based Signal and Favors Cell-to-Cell Viral Transmission", *Journal of Virology*, Jun. 1999; 73(6):5010-5017.

Weiner, David B., et al., "Genetic Vaccines", *Scientific American*, Jul. 1999; 799:1-9.

Liu, Margaret A., "Vaccines in the $21^{st}$ Century", *BMJ*, Nov. 13, 1999; 319:1-4.

Babst, Markus, et al., "Mammalian Tumor Susceptibility Gene 101 (TSG101) and the Yeast Homologue, Vps23p, Both Function in Late Endosomal Trafficking", *Traffic*, 2000; 1:248-258.

NCBI Entrez Protein Database Accession No. AAF35354, Feb. 23, 2000.

Alexander, Louis, et al., "Unusual Polymorphisms in Human Immunodeficiency Virus Type 1 Associated with Nonprogressive Infection", *Journal of Virology*, May 2000; 74(9):4361-4376.

Butkiewicz, Nancy, et al., "Virus-Specific Cofactor Requirement and Chimeric Hepatitis C Virus/GB Virus B Nonstructural Protein 3" *Journal of Virology*, May 2000; 74(9):4291-4301.

Accola, Molly A., et al., "Efficient Particle Production by Minimal Gag Constructs Which Retain the Carboxy-Terminal Domain of Human Immunodeficiency Virus Type 1 Capsid-p2 and a Late Assembly Domain", *Journal of Virology*, Jun. 2000; 74(12):5395-5402.

Yuan, Bing, et al., "Infectivity of Moloney Murine Leukemia Virus Defective in Late Assembly Events Is Restored by Late Assembly Domains of Other Retroviruses", *Journal of Virology*, Aug. 2000; 74(16):7250-7260.

Hermida-Matsumoto, Luz, et al., "Localization of Human Immunodeficiency Virus Type 1 Gag and Env at the Plasma Membrane by Confocal Imaging" *Journal of Virology*, Sep. 2000: 74(18):8670-8679.

NCBI Entrez Protein Database Accession No. CAB92786, Sep. 20, 2000.

Barouch, Dan H., et al., "Control of Viremia and Prevention of Clinical AIDS in Rhesus Monkeys by Cytokine-Augmented DNA Vaccination", *Science*, Oct. 20, 2000; 290:486-492.

Jayakar, Himangi R., et al., "Mutations in the PPPY Motif of Vesicular Stomatitis Virus Matrix Protein Reduce Virus Budding by Inhibiting a Late Step in Virion Release", *Journal of Virology*, Nov. 2000: 74(21):9818-9827.

Patnaik, Akash, et al., "Ubiquitin is part of the retrovirus budding machinery", *PNAS*, Nov. 21, 2000: 97(24):13069-13074.

Schubert, Ulrich, et al., "Proteasome inhibition interferes with Gag polyprotein processing, release, and maturation of HIV-1 and HIV-2", *PNAS*, Nov. 21, 2000; 97(24):13057-13062.

Strack, Bettina, et al., "A role for ubiquitin ligase recruitment in retrovirus release", *PNAS*, Nov. 21, 2000; 97(24):13063-13068.

Vogt, Volker M., "Ubiquitin in retrovirus assembly: Actor or bystander?", *PNAS*, Nov. 21, 2000; 97(24):12945-12947.

Harty, Ronald N., et al., "A PpxY motif within the VP40 protein of Ebola virus interacts physically and functionally with a ubiquitin ligase: Implications for filovirus budding", *PNAS*, Dec. 5, 2000; 97(25):13871-13876.

Amara, Rama Rao, et al., "Control of a Mucosal Challenge and Prevention of AIDS by a Multiprotein DNA/MVA Vaccine", *Science*, Apr. 6, 2001; 292:69-74.

Bishop, Naomi, et al., "TSG101/Mammalian VPS23 and Mammalian VPS28 Interact Directly and Are Recruited to VPS4-induced Endosomes", *The Journal of Biological Chemistry*, Apr. 13, 2001; 276(15):11735-11742.

NCBI Entrez Protein Database Accession No. AAD17020, Jun. 1, 2001.

Verplank, Lynn, et al., "Tsg101, a homologue of ubiquitin-conjugating (E2) enzymes, binds the L domain in HIV type 1 $Pr55^{Gag}$", *PNAS*, Jul. 3, 2001; 98(14):7724-7729.

Rose, Nina F., et al., "An Effective AIDS Vaccine Based on Live Attenuated Vesicular Stomatitis Virus Recombinants", *Cell*, Sep. 7, 2001; 106:539-549.

Garrus, Jennifer E., et al., "Tsg101 and the Vacuolar Protein Sorting Pathway Are Essential for HIV-1 Budding", *Cell*, Oct. 5, 2001; 107:55-65.

Luban, Jeremy, "HIV-1 and Ebola virus: The getaway driver nabbed", *Nature Medicine*, Dec. 2001; 7(12):1278-1280.

Martin-Serrano, Juan, et al., "HIV-1 and Ebola virus encode small peptide motifs that recruit Tsg101 to sites of particle assembly to facilitate egress", *Nature Medicine*, Dec. 2001; 7(12):1313-1319.

Pornillos, Owen, et al., "Structure and functional interactions of the Tsg101 UEV domain", *The EMBO Journal*, 2002; 21(10):2397-2406.

Demirov, Dimiter G., et al., "Overexpression of the N-Terminal domain of TSG101 inhibits HIV-1 budding by blocking late domain function", *PNAS*, Jan. 22, 2002; 99(2):955-960.

Carter, Carol A, "Tsg101: HIV-1's ticket to ride", *Trends in Microbiology*, May 2002; 10(5):203-205.

Myers, Erin L., et al., "Tsg101, an Inactive Homologue of Ubiquitin Ligase E2, Interacts Specifically with Human Immunodeficiency Virus Type 2 Gag Polyprotein and Results in Increased Levels of Ubiquitinated Gag", *Journal of Virology*, Nov. 2002; 76(22):11226-11235.

Pornillos, Owen, et al., "Structure of the Tsg101 UEV domain in complex with the PTAP motif of the HIV-1 p6 protein", *Nature Structural Biology*, Nov. 2002; 9(11):812-817.

\* cited by examiner

IMMUNIZING COMPOSITIONS COMPRISING HIV-1 PROVIRAL CONSTRUCTS WITH AN INACTIVE P6 GAG TSG101 UEV BINDING DOMAIN CAPABLE OF PRODUCING BUDDING-DEFECTIVE VIRAL PARTICLES THAT REMAIN TETHERED TO THE CELL SURFACE

CROSS-REFERENCE TO RELATED U.S. APPLICATION

This application claims the benefit (under 35 U.S.C. §119 (e)) of U.S. Provisional Application No. 60/342,692 filed on Dec. 21, 2001, which is incorporated herein by reference in its entirety.

FIELD OF THE INVENTION

The present invention generally relates to treating and preventing diseases, particularly to methods and compositions for treating and preventing HIV infection and AIDS.

BACKGROUND OF THE INVENTION

Human immunodeficiency virus (HIV) infection causes the acquired immunodeficiency syndrome (commonly known as AIDS). HIV is a retrovirus that primarily infects T cells expressing the CD4 glycoprotein, i.e., $CD4^+$ T-cells, which are also known as helper T-cells. HIV virus multiplies in helper T-cells and destroys the host helper T-cells, resulting in cellular immunity depression and leaving the infected patient susceptible to opportunistic infections, malignancies and various other pathological conditions. Ultimately, HIV infection can cause depletion of helper T-cells and collapse of a patient's immune defenses. Not surprisingly, HIV-infected individuals and AIDS patients typically develop AIDS-related conditions such as AIDS-related complex (ARC), progressive generalized lymphadenopathy (PGL), dementia, tropical paraparesis, Kaposi's sarcoma, thrombocytopenia purpurea, herpes infection, cytomegalovirus infection, Epstein-Barr virus related lymphomas among others. In any case, the HIV viruses in an infected individual are infectious and can be transmitted to other people through blood transfusion or sexual contacts.

Efforts have been made in the past fifteen years or so in developing vaccines for treating or preventing HIV infection and AIDS. Various forms of vaccines have been proposed and tested in animal models or humans. These include whole killed and live-attenuated HIV viruses, recombinant viral particles, recombinant viral or bacterial vectors capable of expressing antigenic HIV proteins, recombinant HIV proteins, and DNA vaccines. However, none has successfully passed clinical testing.

There has also been a great deal of effort in developing pharmaceutical compounds for treating HIV infection and AIDS. The therapeutic approaches have been mostly focused on a limited number of drug targets, namely HIV reverse transcriptase, HIV protease, and HIV integrase. A number of reverse transcriptase inhibitors and protease inhibitors have been developed or marketed. Examples of nucleoside reverse transcriptase inhibitors include Zidovudine, Stavudine, Lamivudine, and ddI. Examples of non-nucleoside reverse transcriptase inhibitors include Efavirenz, Delavirdine, and Abacavir. In addition, a number of HIV protease inhibitors are commercially available including Ritonavir, Nelfinavir, Indinavir and Saquinavir.

However, HIV typically undergoes active mutations as it multiplies. In addition, there are extensive genetic variations in HIV partly due to high mutation rate. Therefore, mutations in HIV reverse transcriptase and protease arise frequently in infected individuals and render the virus resistant to the inhibitor administered to the individuals. Combination therapy, generally referred to as HAART (highly active anti-retroviral therapy), has been developed in which a combination of different anti-HIV inhibitors is administered to a patient. However, viral resistance to combination therapies still frequently develops. In addition, many of the anti-HIV compounds known in the art have other serious drawbacks. For example, the reverse transcriptase inhibitors such as AZT and ddI are fairly toxic and cause serious side effects in patients treated with such compounds.

Therefore, although limited success for controlling HIV infection and AIDS has been achieved with previously developed anti-HIV compounds, there is a need for alternative therapeutic and prophylactic methods that overcome the shortcomings of currently available approaches.

SUMMARY OF THE INVENTION

The present invention provides methods for preventing and treating HIV infection and AIDS by introducing cells displaying HIV late-domain phenotype into a patient, or by causing the formation of cells displaying HIV late-domain phenotype in a patient.

Cells displaying HIV late-domain phenotype have immature non-infectious HIV viral particles incapable of budding off the cell surface but tethered to the cells or to other immature non-infectious HIV viral particles by thin membrane stalks. Such interconnected immature viral particles help to maintain a high concentration of HIV proteins near the cell surface, making the cells immunogenic and particularly effective in stimulating cytotoxic T lymphocytes (CTL) response, which has been recognized to be an essential immune response for inhibiting HIV replication.

In one embodiment, the method of the present invention comprises causing the formation, in a patient's body, of cells displaying HIV late-domain phenotype by administering to the patient in need of therapeutic or prophylactic treatment a mutant HIV Pr55 GAG polypeptide that is sufficient for viral particle assembly but is capable of causing late-domain phenotype in cells, or by administering to the patient a nucleic acid encoding such a mutant HIV Pr55 GAG polypeptide. For example, a mutant HIV Pr55 GAG polypeptide which is sufficient for viral particle assembly but causes late-domain phenotype in cells can be provided by nullifying the late-domain motif of a wild-type or modified HIV Pr55 GAG polypeptide that is capable of mediating virus-like particle assembly. Preferably, a nucleic acid encoding a mutant HIV Pr55 GAG polypeptide sufficient for viral particle assembly but devoid of late domain motifs is incorporated into a plasmid vector which is injected directly into a patient. The nucleic acid can also be delivered into a patient by infecting the patient with a recombinant live vector (e.g., recombinant viral or bacterial vector) carrying the nucleic acid. Preferably, the nucleic acid is administered to a patient by gene gun or powder jet or an equivalent device thereof. In a preferred embodiment, the nucleic acid encoding the mutant HIV Pr55 GAG polypeptide has a nucleotide sequence such that the expression of the mutant polypeptide is Rev-independent.

A compound capable of disrupting or interfering with the protein-protein interaction between the host protein Tsg101 and HIV GAGp6 can also be administered to a patient. In the presence of HIV infection, the compound can cause the formation of cells displaying HIV late-domain phenotype. In preferred embodiments, the compound capable of interfering with the interaction between Tsg101 and HIV GAGp6 comprises an amino acid sequence motif of $PX_1X_2P$ and capable of binding the UEV domain of Tsg 101, wherein $X_1$ and $X_2$ are amino acids. For example, the compound administered can have the amino acid sequence motif of $PX_1X_2P$, wherein $X_1$ is selected from the group consisting of threonine, serine, and isoleucine, and $X_2$ is alanine or threonine.

In accordance with another aspect of the present invention, a method for treating and/or preventing HIV infection and AIDS is provided comprising administering to a patient in need of treatment cells displaying HIV late-domain phenotype. That is, cells displaying HIV late-domain phenotype are prepared in vitro and delivered to a patient in need of treatment.

In preferred embodiments of the methods of the present invention, an adjuvant capable of stimulating immune response is also administered to a patient who is treated with cells displaying HIV late domain phenotype or with a compound (nucleic acids, polypeptides or small organic compounds) capable of causing the formation, in a patient's body, of cells displaying HIV late domain phenotype. In particular, the administration of an adjuvant capable of enhancing cytotoxic T lymphocytes (CTL) response will significantly bolster the anti-HIV immune response in the patient and result in significantly greater treatment efficacy than the administration of the cells or compounds alone.

Suitable adjuvants include, but are not limited to, alum, MF59, LTR72 (a mutant of *E. coli* heat-labile enterotoxin with partial knockout of ADP-ribosyltransferase activity), polyphosphazine adjuvant, interleukins such as IL-1, IL-2, IL-4, IL-6, IL-8, IL-10 and IL-12, interferons such as alpha-interferon and gamma-interferon, tumor necrosis factor (TNF), platelet derived growth factor (PDGF), GCSF, granulocyte-macrophage colony-stimulating factor (GM-CSF), epidermal growth factor (EGF), and the like. Examples of adjuvants capable of stimulating cellular immune responses include cytokines secreted by helper T cells called Th1 cells, e.g., interleukin-2 (IL-2), interleukin-4, interleukin-12 (IL-12) and interleukin-18, fusion proteins having one of such Th1 type cytokines (e.g., IL-2) fused to the Fc portion of immunoglobulin G (IgG), interferons such as alpha-interferon, beta-interferon and gamma-interferon, and chemokines that attract T cells to infected tissues. Non-coding, ISS-enriched plasmid DNAs or ISS oligonucleotides (ISS-ODNs) can also be used in the present invention as adjuvants to enhance cellular immunity.

In a preferred embodiment, a protein adjuvant is used along with a nucleic acid encoding a mutant HIV Pr55 GAG polypeptide sufficient for viral particle assembly but devoid of late domain motifs. In particular, a nucleic acid encoding a protein adjuvant capable of enhancing CTL response is administered together with the nucleic acid encoding a mutant HIV Pr55 GAG polypeptide sufficient for viral particle assembly but devoid of late domain motifs. The two nucleic acids can be incorporated in different expression vectors. However, most preferably, the two nucleic acids are carried within the same expression vector.

In another aspect of the present invention, methods of combination treatment (prophylactic or therapeutic) for treating and/or preventing HIV infection and AIDS are provided. In such methods, both an active agent of the present invention (cells, nucleic acids, polypeptides or small organic compounds, in the presence or absence of an adjuvant) and one or more other known anti-HIV agents are administered to a patient in need of treatment. Such other anti-HIV agents should be pharmaceutically compatible with the active agents of the present invention. Therapeutic compounds known in the art suitable for use in combination therapies include, but are not limited to, HIV protease inhibitors, nucleoside HIV reverse transcriptase inhibitors, non-nucleoside HIV reverse transcriptase inhibitors, and HIV integrase inhibitors. Prophylactic agents known in the art may be also used in combination therapies. Examples of known prophylactic agents include, but are not limited to, inactivated whole HIV viruses, HIV virus-like particles, HIV proteins and nucleic acids encoding HIV proteins such as gp41, gp120, gp160, gag polypeptide, pol products, protease, Nef, Vpr, Vpu, Tat1, Tat2, reverse transcriptase, integrase, Vif, etc.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

BRIEF DESCRIPTION OF THE DRAWINGS

FIG. 1 is a schematic diagram of the wild-type HIV Pr55 GAG polypeptide;

FIG. 2 is a schematic diagram of an example of a mutant HIV Pr55 GAG polypeptide according to the present invention;

FIG. 3 shows a competitive inhibition curve reporting results of experiment described in Example 2 below. Demonstrates competitive inhibition by p6(1-14) of the interaction between GAGp6 and Tsg101;

FIGS. 4 and 5 are Dixon plots of results of experiment described in Example 2 below. Show the nature of p6(1-14) inhibition of interaction between GAGp6 and Tsg101;

FIG. 6 is a plot showing results of Experiment 4 below, reporting relative efficacy of MPI-PEP1 in inhibiting viral reproduction;

FIG. 7 is a plot showing results of Experiment 4 below, reporting relative efficacy of MPI-PEP2 in inhibiting viral reproduction;

FIG. 8 is a plot showing results of Experiment 4 below, reporting relative efficacy of MPI-PEP3 in inhibiting viral reproduction; and FIG. 9 is a plot showing results of Experiment 4 below, reporting relative efficacy of AZT in inhibiting viral reproduction.

DETAILED DESCRIPTION OF THE INVENTION

As used herein, the term "HIV infection" generally encompasses infection of a host animal, particularly a human host, by the human immunodeficiency virus (HIV) family of retroviruses including, but not limited to, HIV I, HIV II, HIV III, LAV-1, LAV-2, and the like. "HIV" can be used herein to refer to any strains, forms, subtypes, clades and variations in the HIV family. Thus, treating HIV infection will encompass the treatment of a person who is a carrier of any of the HIV family of retroviruses or a person who is diagnosed of active AIDS, as well as the treatment or prophylaxis of the AIDS-related conditions in such persons. A carrier of HIV may be identified by any methods known in the art. For example, a person can be identified as an HIV carrier on the basis that the person is anti-HIV antibody positive, or is HIV-positive, or has symptoms of AIDS. That is, "treating HIV infection" should be understood as treating a patient who is at any one of the several stages of HIV infection progression, which, for example, include acute primary infection syndrome (which can be asymptomatic or associated with an influenza-like illness with fevers, malaise, diarrhea and neurologic symptoms such as headache), asymptomatic infection (which is the long latent period with a gradual decline in the number of circulating $CD^{4+}$ T cells), and AIDS (which is defined by more serious AIDS-defining illnesses and/or a decline in the circulating CD4 cell count to below a level that is compatible with effective immune function). In addition, "treating or preventing HIV infection" will also encompass treating suspected infection by HIV after suspected past exposure to HIV by e.g., contact with HIV-contaminated blood, blood transfusion, exchange of body fluids, "unsafe" sex with an infected person, accidental needle stick, receiving a tattoo or acupuncture with contaminated instruments, or transmission of the virus from a mother to a baby during pregnancy, delivery or shortly thereafter. The term "treating HIV infection" may also encompass treating a person who is free of HIV infection but is believed to be at risk of infection by HIV.

The term "treating AIDS" means treating a patient who exhibits more serious AIDS-defining illnesses and/or a decline in the circulating CD4 cell count to below a level that is compatible with effective immune function. The term "treating AIDS" also encompasses treating AIDS-related conditions, which means disorders and diseases incidental to or associated with AIDS or HIV infection such as AIDS-related complex (ARC), progressive generalized lymphadenopathy (PGL), anti-HIV antibody positive conditions, and HIV-positive conditions, AIDS-related neurological conditions (such as dementia or tropical paraparesis), Kaposi's sarcoma, thrombocytopenia purpurea and associated opportunistic infections such as *Pneumocystis carinii* pneumonia, *Mycobacterial tuberculosis*, esophageal candidiasis, toxoplasmosis of the brain, CMV retinitis, HIV-related encephalopathy, HIV-related wasting syndrome, etc.

Thus, the term "preventing AIDS" as used herein means preventing in a patient who has HIV infection or is suspected to have HIV infection or is at risk of HIV infection from developing AIDS (which is characterized by more serious AIDS-defining illnesses and/or a decline in the circulating CD4 cell count to below a level that is compatible with effective immune function) and/or AIDS-related conditions.

The terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, etc. Modifications also include intra-molecular crosslinking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by genes may also be included in a polypeptide.

Unless otherwise specified, the term "Tsg101" as used herein means human Tsg101 protein. Unless otherwise specified, the term "HIV GAGp6" as used herein means the GAGp6 protein of any strain or Glade or subtype of any member of the HIV family, and the term "HIV Pr55 GAG" means the GAG polypeptide of any strain or clade or subtype of any member of the HIV family.

The methods of the present invention for treating HIV infection and/or preventing AIDS comprise a step of introducing cells displaying the HIV late-domain phenotype into a patient, or causing the formation of cells displaying the HIV late-domain phenotype in a patient. The methods can be used in either prophylactic or therapeutic treatment. However, it is believed to be more effective when applied to a patient having HIV infection in a therapeutic approach.

As used herein, the phrase "cells displaying HIV late-domain phenotype" means cells having immature non-infectious HIV viral particles that are incapable of completing the viral budding process, i.e., incapable of budding off the cell surface. The immature non-infectious HIV viral particles are typically tethered to the host cells or to other immature non-infectious HIV viral particles by thin membrane stalks, thus forming clusters of interconnected particles on the surface of the host cells. See Huang et al., *J. Virol.*, 69:6810-6818 (1995). As a result, a large amount of HIV proteins are trapped within the immature viral particles displayed on the surface of the cells. While not wishing to be bound by any theories or hypothesis, it is believed that it is the aggregates of immature viral particles with a large amount of viral proteins that make the cells particularly immunogenic. The cells displaying HIV late-domain phenotype will be particularly effective in eliciting cellular immune responses against HIV viruses and thus are useful as preventive and/or therapeutic vaccines for preventing and/or treating HIV infection and AIDS.

1. Formation of Immunogenic Cells In Vivo

Thus, in a first aspect of the present invention, the methods for treating and/or preventing HIV infection or AIDS include a step of causing, in a patient, the formation of cells displaying HIV late-domain phenotype. According to this aspect of the invention, cells displaying HIV late-domain phenotype are formed within a patient's body. Once such cells are formed, they stimulate the patient's immune system and elicit cellular immune responses against HIV viruses. In addition, they may also be able to cause humoral responses in the patient against the HIV viral proteins carried by the cells thus producing antibodies against the HIV viral proteins.

Any methods for causing the formation of cells displaying HIV late-domain phenotype in a patient can be used for purposes of this aspect of the present invention.

In some embodiments, the formation of cells displaying HIV late-domain phenotype in a patient can be achieved by administering to a patient in need of treatment a mutant HIV Pr55 GAG polypeptide which is sufficient for viral particle assembly but is capable of causing HIV late-domain phenotype in cells, or by administering to a patient a nucleic acid encoding a mutant HIV Pr55 GAG polypeptide which is sufficient for viral particle assembly but is capable of causing HIV late-domain phenotype in cells.

In HIV-infected cells, HIV Pr55 GAG is a polypeptide synthesized on cytoplasmic polysomes and targeted to the plasma membrane thereafter. Once Pr55 GAG is anchored to the plasma membrane, it oligomerizes and assembles into immature virus-like particles, and also initiates and completes the viral budding process. During the maturation process, the Pr55 GAG polypeptide in the immature viral particle is cleaved by HIV protease, giving rise to a set of mature proteins. Such mature proteins include matrix (MA), capsid (CA), nucleocapsid (NC), and GAGp6. The matrix domain contains an N-terminal myristylation signal (which is required for the covalent attachment of myristic acid to the N-terminus of MA and for Pr55 GAG membrane binding and particle formation). In the mature virus particle the matrix (MA) forms a shell underneath the cell-derived lipid envelope, which is the outer layer of the virion particle. The capsid domain (CA) participates in protein-protein interactions in virion assembly and mature capsid forms the core shell in the infectious virus. CA contains an N-terminal CA domain, the major homology region (MHR), an interdomain connector region therebetween, and a C-terminal CA domain. In mature viral particles, the nucleocapsid (NC) is associated with the genomic RNA within the core. The GAGp6 domain is at the C-terminus of the Pr55 GAG polypeptide and contains a late domain motif that is required for the completion of viral budding. The Pr55 GAG polypeptide also contains two additional small domains, p2 and p1, which are located between the C-terminal CA domain and NC, and between NC and GAGp6, respectively. See Vogt, *Proc. Natl. Acad. Sci. USA*, 97(24):12945-7 (2000). A schematic diagram of the HIV Pr55 GAG polypeptide is shown in FIG. 1 with relevant domains indicated.

A wild-type HIV Pr55 GAG polypeptide, when expressed alone and in the absence of any other viral proteins, is sufficient to mediate the formation of virus-like particles, which are released from the host cell. See e.g., Gheysen et al., *Cell*, 59:103-112 (1989). In addition, it has been known that not all domains of Pr55 GAG polypeptide are required for the assembly and release of virus-like particles. See Accola et al., *J. Virol.*, 74:5395-5402 (2000); Borsetti et al., *J. Virol.*, 72:9313-9317 (1998); Reil et al., *EMBO J.*, 17:2699-2708 (1998); Zhang et al., *J. Virol.*, 72:1782-1789 (1998); Recin et al., *J. Virol.*, 70:8645-8652 (1996); Recin et al., *J. Virol.*, 69:642-650 (1995); Dorfman et al., *J. Virol.*, 68:8180-8187 (1994); Lee et al., *J. Virol.*, 68:6644-6654 (1994); Wang et al., *J. Virol.*, 67:7067-7076 (1993); and Wang et al., *J. Virol.*, 67:4264-4273 (1993), all of which are incorporated herein by reference.

Accordingly, a mutant HIV Pr55 GAG polypeptide that is sufficient for viral particle assembly but causes HIV late-domain phenotype in cells can be provided based on any of the wild-type or modified HIV Pr55 GAG polypeptides known in the art to be sufficient for the assembly of virus-like particles, some of which are disclosed in the references cited above. Specifically, a mutant HIV Pr55 GAG polypeptide which is sufficient for viral particle assembly but causes late-domain phenotype in cells can be generated by modifying such wild-type or modified HIV Pr55 GAG polypeptides such that they can mediate virus-like particle assembly but cause HIV late-domain phenotype when expressed in a host cell.

GAGp6 contains a late domain, so-called because it is required for a late stage of HIV viral budding from the host cell surface. See Huang et al., *J. Virol.,* 69:6810-6818 (1995). Specifically, late domain-deficient HIV viruses proceed through the typical stages of virus morphogenesis but fail to complete the process. Rather, they remain tethered to the plasma membrane and are thus rendered non-infectious. That is, the viral budding process is stalled, and the host cell displays late-domain phenotype. See Huang et al., *J. Virol.,* 69:6810-6818 (1995).

Thus, in one embodiment, a mutant HIV Pr55 GAG polypeptide that is sufficient for virus-like particle assembly but causes late-domain phenotype in cells can be provided by modifying a wild-type HIV Pr55 GAG polypeptide to nullify the functional late domain therein. Also, if a modified HIV Pr55 GAG polypeptide sufficient for virus-like particle assembly contains a functional late domain, that late domain can be nullified to provide a mutant HIV Pr55 GAG polypeptide that is sufficient for viral particle assembly but causes late-domain phenotype in cells.

Typically, the late domain in HIV Pr55 GAG has the P(T/S)AP (SEQ ID NO:1 or SEQ ID NO:2) sequence motif in the GAGp6 domain. The P(T/S)AP (SEQ ID NO:1 or SEQ ID NO:2) sequence motif binds the UEV domain of Tsg101 in the host cell. The binding of the P(T/S)AP (SEQ ID NO:1 or SEQ ID NO:2) sequence motif to Tsg101 is required for HIV viral budding from the host cell surface. Mutations in the P(T/S)AP (SEQ ID NO:1 or SEQ ID NO:2) sequence motif that abolish the binding lead to HIV late-domain phenotype.

For purposes of the present invention, the HIV late domain in a wild-type or modified HIV Pr55 GAG polypeptide can be nullified by any means so long as the resultant polypeptide is incapable of binding Tsg101, particularly the UEV domain of Tsg101. In one embodiment, the functional late domain can be nullified simply by deleting the entire P(T/S)AP (SEQ ID NO:1 or SEQ ID NO:2) sequence motif in a wild-type or modified HIV Pr55 GAG polypeptide. Alternatively, amino acid substitution mutations in or near the P(T/S)AP (SEQ ID NO:1 or SEQ ID NO:2) sequence motif can be created so that the resultant HIV Pr55 GAG polypeptide is incapable of binding Tsg101. For example, as disclosed in commonly assigned U.S. Provisional Application Ser. No. 60/276,259, substitution of the amino acid leucine (L) for the first amino acid P in the P(T/S)AP (SEQ ID NO:1 or SEQ ID NO:2) sequence motif, substitution of the amino acid arginine (R) for the third amino acid A in the P(T/S)AP (SEQ ID NO:1 or SEQ ID NO:2) sequence motif, and substitution of the amino acid leucine (L) for the last amino acid P in the P(T/S)AP (SEQ ID NO:1 or SEQ ID NO:2) sequence motif each individually abolishes the GAGp6 binding affinity to Tsg101. The same mutations in the PTAP (SEQ ID NO:1) motif of the HIV GAGp6 gag protein prevent HIV particles from budding off the host cell surface. See Huang et al., *J. Virol.,* 69:6810-6818 (1995). Additionally, deletion of one, two or three of the four amino acids in the P(T/S)AP (SEQ ID NO:1 or SEQ ID NO:2) sequence motif should also lead to the abolishment of the binding affinity of an HIV Pr55 GAG polypeptide to Tsg101 and cause late-domain phenotype in the host cells. Insertion of amino acids into the P(T/S)AP (SEQ ID NO:1 or SEQ ID NO:2) sequence motif may also be useful. Further, a combination of deletion, insertion and/or substitution mutations can also nullify the HIV late domain. Deletions, insertions and substitutions can be achieved by standard molecular biology techniques or created during standard chemical synthesis of the proteins, as will be apparent to skilled artisans.

As is known in the art, distinct late domains have been identified in the structural proteins of several other enveloped viruses. See Vogt, *Proc. Natl. Acad. Sci. USA,* 97:12945-12947 (2000). Two well-characterized late domains are the "PY" motif (consensus sequence: PPXY; X=any amino acid) found in membrane-associated proteins from certain enveloped viruses. See Craven et al., *J. Virol.,* 73:3359-3365 (1999); Harty et al., *Proc. Natl. Acad. Sci. USA,* 97:13871-13876 (2000); Harty et al., *J. Virol.,* 73:2921-2929 (1999); and Jayakar et al., *J. Virol.,* 74:9818-9827 (2000). The cellular target for the PY motif is Nedd4 which also contains a Hect ubiquitin E3 ligase domain. The "YL" motif (YPDL or YxxL) was found in the GAG protein of equine infectious anemia virus (EIAV). Puffer et al., *J. Virol.,* 71:6541-6546 (1997); Puffer et al., *J. Virol.,* 72:10218-10221 (1998). The cellular receptor for the "YL" motif appears to be the AP-50 subunit of AP-2. Puffer et al., *J. Virol.,* 72:10218-10221 (1998). Interestingly, the late domains such as the P(T/S)AP (SEQ ID NO:1 or SEQ ID NO:2) motif, PY motif and the YL motif can still function when moved to different positions within retroviral GAG proteins. Parent et al., *J. Virol.,* 69:5455-5460 (1995); Yuan et al., *EMBO J.,* 18:4700-4710 (2000). More-over, the late domains such as the P(T/S)AP (SEQ ID NO:1 or SEQ ID NO:2) motif, PY motif and the YL motif can function interchangeably. That is, one late domain motif can be used in place of another late domain motif without affecting viral budding. Parent et al., *J. Virol.,* 69:5455-5460 (1995); Yuan et al., *EMBO J.,* 18:4700-4710 (2000); Strack et al., *Proc. Natl. Acad. Sci. USA,* 97:13063-13068 (2000). Accordingly, in providing a mutant HIV Pr55 GAG polypeptide that is sufficient for viral particle assembly but causes late-domain phenotype in cells, it is important that no such PY motif, YL motif or new P(T/S)AP (SEQ ID NO:1 or SEQ ID NO:2) motif is created anywhere in the HIV Pr55 GAG polypeptide. That is, the mutant HIV Pr55 GAG polypeptide should be devoid of late-domain motifs. As used herein, the term "devoid of late-domain motifs" is intended to mean that the mutant GAG polypeptide does not contain any late domain motifs, i.e., any amino acid sequence that, when placed in a mutant HIV Pr55 GAG polypeptide that otherwise cannot drive the budding of viral particles from the host cell surface, is sufficient to enable the virus-like particles formed by the HIV Pr55 GAG polypeptide having the amino acid sequence to bud off the host cell plasma membrane into the extracellular space.

Figure 2:
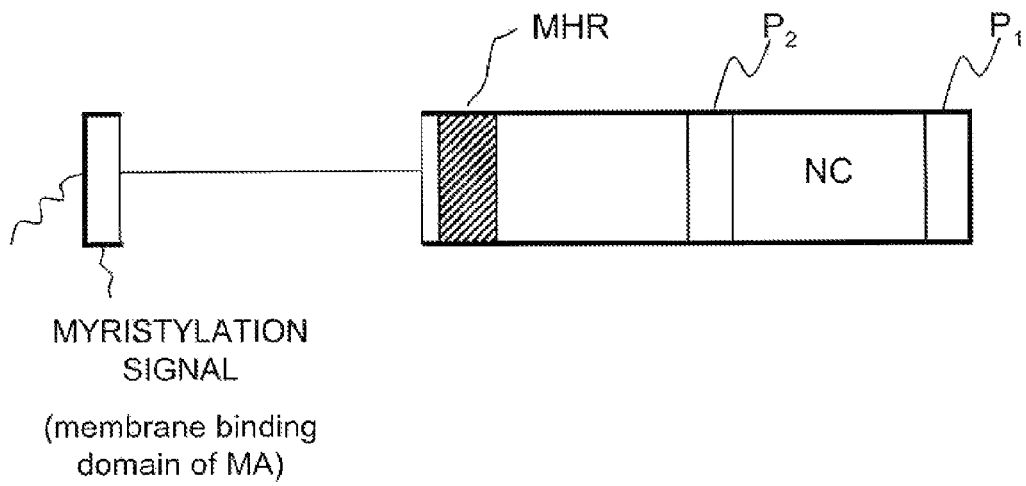

For example, the mutant HIV Pr55 GAG polypeptides of the present invention may include at least the following regions from a wild-type HIV Pr55 GAG polypeptide: (1) the membrane binding domain of HIV Pr55 GAG polypeptide, which includes the N-terminal myristate and a contiguous span of six (6), seven (7) or eight (8) basic amino acids from the N-terminus of a wild-type HIV Pr55 GAG polypeptide (see Zhou et al., *J. Virol.,* 68:2556-2569 (1994), which is incorporated herein by reference), (2) about the C-terminal third of the capsid domain, which includes the major homology region (MHR), (3) the p2 domain, (4) the NC domain, and (5) the p1 domain. The mutant HIV Pr55 GAG polypeptide does not have a late domain motif. Preferably, The mutant HIV Pr55 GAG polypeptide does not have a GAGp6 domain. See FIG. 2. Various variants of such mutant HIV Pr55 GAG polypeptides may also be useful. Such variants may include additional wild-type HIV Pr55 GAG polypeptide sequences, or substitutions of amino acids. Chimeric proteins including the above essential HIV Pr55 GAG regions and some non-HIV sequences (e.g., from other lentiviruses or retroviruses) may also be used. Indeed, one or more non-essential regions or even the essential sequences may be replaced by non-HIV sequences such as their counterparts from other lentiviruses or retroviruses. Essentially, any modifications may be made to a HIV Pr55 GAG polypeptide of the present invention so long as the resultant polypeptide is sufficient for virus-like particle assembly but causes late-domain phenotype in cells.

In another embodiment, a nucleic acid encoding a mutant HIV Pr55 GAG polypeptide that is sufficient for virus-like particle assembly but causes late-domain phenotype in cells is administered to a patient for purposes of preventing and/or treating HIV infection and AIDS. The mutant HIV Pr55 GAG polypeptide encoded by the administered nucleic acid can be in any forms described above.

Thus, any nucleic acid can be used so long as it encodes a mutant HIV Pr55 GAG polypeptide that is sufficient for viral particle assembly but causes late-domain phenotype in cells. It is noted that the nucleic acid can be in the form of DNA or RNA or a modified form, either single-stranded or double-stranded. In one embodiment, a nucleic acid administered to a patient includes nucleotide sequences encoding the portions of a wild-type HIV Pr55 GAG polypeptide that are essential for viral particle assembly but not the P(T/S)AP (SEQ ID NO:1 or SEQ ID NO:2) motif in the GAGp6 domain. For example, the nucleic acid encodes the following regions of a wild-type HIV Pr55 GAG polypeptide but not the P(T/S)AP (SEQ ID NO:1 or SEQ ID NO:2) motif in the GAGp6 domain: (1) the membrane binding domain of HIV Pr55 GAG polypeptide, which includes the N-terminal myristate and a contiguous span of six, seven or eight basic amino acids from the N-terminus of wild-type HIV Pr55 GAG polypeptide, (2) about the C-terminal third of the capsid domain, which includes the major homology region (MHR), (3) the p2 domain, (4) the NC domain, (5) the p1 domain, and (6) the GAGp6 domain deficient of the P(T/S)AP (SEQ ID NO:1 or SEQ ID NO:2) motif. In a specific embodiment, the nucleic acid encodes a polypeptide devoid of the entire GAGp6 domain. In a preferred embodiment, the nucleic acid administered encodes a wild-type HIV Pr55 GAG polypeptide sequence but devoid of the P(T/S)AP (SEQ ID NO:1 or SEQ ID NO:2) motif in the GAGp6 domain. In another preferred embodiment, the nucleic acid administered encodes a wild-type HIV Pr55 GAG polypeptide sequence but devoid of the entire GAGp6 domain.

Although HIV GAG sequences are preferred, a suitable nucleic acid may also encode a chimeric protein having the above essential HIV Pr55 GAG regions and some non-HIV sequences (e.g., from other lentiviruses or retroviruses).

In addition to a nucleic acid encoding mutant HIV Pr55 GAG polypeptide according to the present invention, one or more other HIV proteins, e.g., envelope proteins, POL products, protease, reverse transcriptase, the Vpr protein, Nef, and the like, or immunogenic fragments thereof may also be administered to a patient. Nucleic acids encoding such other HIV proteins may be used together with, or in lieu of, a nucleic acid encoding mutant HIV Pr55 GAG polypeptide. Thus, a DNA or RNA molecule including an HIV genome devoid of the sequence encoding the P(T/S)AP (SEQ ID NO:1 or SEQ ID NO:2) motif in the GAGp6 domain, preferably devoid of the entire sequence encoding the GAGp6 domain can be administered. A nucleic acid containing a portion of an HIV genome that includes the Pr55 GAG-encoding sequence devoid of the sequence encoding the P(T/S)AP (SEQ ID NO:1 or SEQ ID NO:2) motif in the GAGp6 domain, preferably devoid of the entire sequence encoding the GAGp6 domain will also be useful. For example, the nucleic acid can be a modified HIV genome devoid of long term repeats and devoid of the P(T/S)AP (SEQ ID NO:1 or SEQ ID NO:2) motif-encoding sequence. In another example, the nucleic acid is a modified HIV genome devoid of long-term repeats and devoid of GAGp6 domain-encoding sequence. In a preferred embodiment, the nucleic acid is a modified HIV genome that includes the ENV gene and a modified GAG gene devoid of GAGp6 domain-encoding sequence. The nucleic acid encoding the mutant HIV Pr55 GAG polypeptide according to the present invention and the nucleic acid(s) encoding other HIV protein(s) may be linked together and incorporated into the same expression vector. They can also be carried with separate expression vectors. Thus, the present invention also provides a composition that includes one expression vector containing a nucleic acid encoding the mutant HIV Pr55 GAG polypeptide according to the present invention and one or more other expression vectors carrying a nucleic acid encoding another protein, preferably another HIV protein or homologue or immunogenic fragment thereof. Examples of other HIV proteins include, but are limited to, envelop proteins, gag polypeptide (wild-type or mutant), protease, Nef, Vpr, Pol, Vpu, Tat1, Tat2, reverse transcriptase, integrase, Vif, etc.

It has been shown that the native coding sequences for HIV Pr55 GAG, POL, and ENV contain inhibitory/instability sequences (INS), which make the expression of the genes Rev-dependent. Nucleotide substitutions may be introduced into the coding sequences for the GAG, Pol, and Env proteins to inactivate the INSs without causing any amino acid sequence change such that the expression of the genes becomes Rev-independent. Specifically, as disclosed in U.S. Pat. No. 5,965,726, an INS is found in a AT-rich region of the native DNA sequence encoding the matrix domain (also known as p17) of HIV Pr55 GAG. This INS can be inactivated by introducing into this region 28 silent point mutations. Due to codon degeneracy, the mutations change the nucleotide sequence without altering the amino acid sequence in this region. The inactivation of this INS leads to substantially increased production of HIV Pr55 GAG polypeptide in the absence of HIV Rev protein. See Schwartz et al., *J. Virol.*, 66:7176-7182 (1992) and U.S. Pat. No. 5,965,726, both of which are incorporated herein by reference. Accordingly, in preferred embodiments, it is preferable that the nucleic acid of the present invention is capable of expressing a HIV Pr55 GAG mutant polypeptide in the absence of HIV Rev protein. In one embodiment, the native INS in coding sequence for the matrix domain is inactivated by the introduction of multiple point mutations in and/or near the INS. More preferably, all identifiable INSs in the coding sequence for the mutant HIV Pr55 GAG polypeptide of the present invention are inactivated including the INS in the gag-pol region. See Schwartz et al., *J. Virol.*, 66:7176-7182 (1992). When the nucleic acid encoding a mutant HIV Pr55 GAG polypeptide of the present invention also encodes another HIV protein such as Env or Pol, preferably the native INS(s) in the nucleotide sequence corresponding such other protein are also inactivated. Methods for identifying and inactivating INSs are disclosed in Schwartz et al., *J. Virol.*, 66:7176-7182 (1992) and U.S. Pat. No. 5,965,726, both of which are incorporated herein by reference.

The nucleic acid of the present invention encoding a mutant HIV Pr55 GAG polypeptide that is sufficient for viral particle assembly but causes late-domain phenotype in cells can be delivered into a patient by any suitable methods known in the art. For example, the nucleic acid can be delivered by various gene therapy methods known in the art. Successes in gene therapy have been reported recently. See e.g., Kay et al., *Nature Genet.*, 24:257-61 (2000); Cavazzana-Calvo et al., *Science*, 288:669 (2000); and Blaese et al., *Science*, 270: 475 (1995); Kantoff, et al., *J. Exp. Med.*, 166:219 (1987).

Any suitable gene therapy methods may be used for purposes of the present invention. Generally, the exogenous nucleic acid of the present invention is incorporated into a suitable expression vector and is operably linked to a promoter in the vector such that the promoter can drive the transcription from the exogenous nucleic acid. Suitable promoters include but are not limited to viral transcription promoters derived from adenovirus, simian virus 40 (SV40) (e.g., the early and late promoters of SV40), Rous sarcoma virus (RSV), and cytomegalovirus (CMV) (e.g., CMV immediate-early promoter), human immunodeficiency virus (HIV) (e.g., long terminal repeat (LTR)), vaccinia virus (e.g., 7.5K promoter), and herpes simplex virus (HSV) (e.g., thymidine kinase promoter). Where tissue-specific expression of the exogenous gene is desirable, tissue-specific promoters may be operably linked to the exogenous gene. In this regard, a $CD^{4+}$ T cell-specific promoter will be most desirable.

In one embodiment, the exogenous nucleic acid is incorporated into a plasmid DNA vector. Many commercially available expression vectors may be useful for the present invention, including, e.g., pCEP4, pcDNAI, pIND, pSec-Tag2, pVAX1, pcDNA3.1, pBI-EGFP, pBlueScript, and pDisplay. Particularly, the pV1R vector has been successfully used for the expression of SIV GAG and HIV ENV proteins in rhesus monkeys. See e.g., Barouch et al., *Science*, 290:486-492 (2000), which is incorporated herein by reference.

Various viral vectors may also be used. Typically, in a viral vector, the viral genome is engineered to eliminate the disease-causing capability, e.g., the ability to replicate in the host cells. The exogenous nucleic acid to be introduced into a patient may be incorporated into the engineered viral genome, e.g., by inserting it into a viral gene that is non-essential to the viral infectivity. Viral vectors are convenient to use as they can be easily introduced into tissue cells by way of infection. Once in the host cell, the recombinant virus typically is integrated into the genome of the host cell. In rare instances, the recombinant virus may also replicate and remain as extrachromosomal elements.

A large number of retroviral vectors have been developed for gene therapy. These include vectors derived from oncoretroviruses (e.g., MLV), lentiviruses (e.g., HIV and SIV) and other retroviruses. For example, gene therapy vectors have been developed based on murine leukemia virus (See, Cepko, et al., *Cell*, 37:1053-1062 (1984), Cone and Mulligan, *Proc. Natl. Acad. Sci. U.S.A.*, 81:6349-6353 (1984)), mouse mammary tumor virus (See, Salmons et al., *Biochem. Biophys. Res. Commun.*, 159:1191-1198 (1984)), gibbon ape leukemia virus (See, Miller et al., *J. Virology*, 65:2220-2224 (1991)), HIV, (See Shimada et al., *J. Clin. Invest.*, 88:1043-1047 (1991)), and avian retroviruses (See Cosset et al., *J. Virology*, 64:1070-1078 (1990)). In addition, various retroviral vectors are also described in U.S. Pat. Nos. 6,168,916; 6,140,111; 6,096,534; 5,985,655; 5,911,983; 4,980,286; and 4,868,116, all of which are incorporated herein by reference.

Adeno-associated virus (AAV) vectors have been successfully tested in clinical trials. See e.g., Kay et al., *Nature Genet.* 24:257-61 (2000). AAV is a naturally occurring defective virus that requires other viruses such as adenoviruses or herpes viruses as helper viruses. See Muzyczka, *Curr. Top. Microbiol. Immun.*, 158:97 (1992). A recombinant AAV virus useful as a gene therapy vector is disclosed in U.S. Pat. No. 6,153,436, which is incorporated herein by reference.

Adenoviral vectors can also be useful for purposes of delivering the exogenous nucleic acid in accordance with the present invention. For example, U.S. Pat. No. 6,001,816 discloses an adenoviral vector, which is used to deliver a leptin gene intravenously to a mammal to treat obesity. Other recombinant adenoviral vectors may also be used, which include those disclosed in U.S. Pat. Nos. 6,171,855; 6,140, 087; 6,063,622; 6,033,908; and 5,932,210, and Rosenfeld et al., *Science*, 252:431-434 (1991); and Rosenfeld et al., *Cell*, 68:143-155 (1992).

Other useful viral vectors include recombinant hepatitis viral vectors (See, e.g., U.S. Pat. No. 5,981,274), and recombinant entomopox vectors (See, e.g., U.S. Pat. Nos. 5,721,352 and 5,753,258). In addition, alphavirus vectors may also be desirable. Alphaviruses are positive stranded RNA viruses. The sequence encoding replica structural proteins can be replaced by the exogenous nucleic acid. The alphavirus vectors carrying the exogenous nucleic acid can be targeted to dendritic cells to facilitate the stimulation of cytotoxic T lymphocytes. See Polo et al., *Proc. Natl. Acad. Sci. USA*, 96:4598-4603 (1996).

In addition to viral vectors, bacterial vectors can also be used. That is, the exogenous nucleic acid to be delivered can be incorporated into attenuated bacteria such as attenuated *salmonella* and *shigella*. See Levine et al., *J. Biotechnol.*, 44:193-196 (1996); Tacket et al., *Infect. Immun.*, 65:3381-3385 (1997); and Sizemore et al., *Vaccine*, 15:804-807 (1997).

The exogenous nucleic acid itself or a plasmid or viral or other expression vector carrying the exogenous nucleic acid can be introduced into a patient by various methods known in the art. For example, as will apparent to skilled artisans, the exogenous nucleic acid incorporated into a viral or bacterial vector can be administered to patients by direct infection. The nucleic acid carried by plasmid vectors can be used as DNA or RNA vaccines, i.e., in the form of naked DNA or RNA, that are administered directly into an appropriate tissue or organ of a patient. The naked DNA or RNA can be delivered by injection into skin, muscle or other tissues. Alternatively, a gene gun or an equivalent device thereof can be used for delivery into skin or mucous membrane or other tissues. Some success has been achieved using such genetic vaccines in the art. The use of this approach for purposes of the present invention will be apparent to a skilled artisan apprised of the present disclosure. See Ulmer et al., *Science*, 259:1745 (1993); Weiner & Kennedy, *Scientific American*, July, 1999; Barouch et al., *Science*, 290:486-492 (2000), all of which are incorporated herein by reference.

Alternatively, catheters or like devices may be used for delivery into a target organ or tissue. Suitable catheters are disclosed in, e.g., U.S. Pat. Nos. 4,186,745; 5,397,307; 5,547,472; 5,674,192; and 6,129,705, all of which are incorporated herein by reference.

Other non-traditional vectors may also be used for purposes of this invention. For example, International Publication No. WO 94/18834 discloses a method of delivering DNA into mammalian cells by conjugating the DNA to be delivered with a polyelectrolyte to form a complex. The complex may be microinjected into or taken up by cells.

The exogenous nucleic acid or plasmid DNA vector containing the exogenous gene may also be introduced into cells by way of receptor-mediated endocytosis. See e.g., U.S. Pat. No. 6,090,619; Wu and Wu, *J. Biol. Chem.*, 263:14621 (1988); Curiel et al., *Proc. Natl. Acad. Sci. USA*, 88:8850 (1991). For example, U.S. Pat. No. 6,083,741 discloses introducing an exogenous nucleic acid into mammalian cells by associating the nucleic acid to a polycation moiety (e.g., poly-L-lysine, having 3-100 lysine residues), which is itself coupled to an integrin receptor binding moiety (e.g., a cyclic peptide having the amino acid sequence RGD).

Alternatively, the exogenous nucleic acid or vectors containing it can also be delivered into cells via amphiphiles. See e.g., U.S. Pat. No. 6,071,890. Typically, the exogenous nucleic acid or a vector containing the nucleic acid forms a complex with the cationic amphiphile. Cells in a patient's body contacted with the complex can readily absorb the complex.

To deliver the mutant HIV Pr55 GAG polypeptides or other peptide compounds into cells in a patient's body, the mutant HIV Pr55 GAG polypeptides or peptide compounds are preferably associated with a "transporter" capable of increasing the uptake of the peptides by human cells. It is noted that the compound administered to cells in vitro or in vivo in the method of the present invention preferably is delivered into the cells in order to achieve optimal results. Thus, preferably, the compound to be delivered is associated with a transporter capable of increasing the uptake of the compound by a human cell. As used herein, the term "associated with" means a compound to be delivered is physically associated with a transporter. The compound and the transporter can be covalently linked together, or associated with each other as a result of physical affinities such as forces caused by electrical charge differences, hydrophobicity, hydrogen bonds, van der Waals force, ionic force, or a combination thereof. For example, the compound can be encapsulated within a transporter such as a cationic liposome.

As used herein, the term "transporter" refers to an entity (e.g., a compound or a composition or a physical structure formed from multiple copies of a compound or multiple different compounds) that is capable of facilitating the uptake of a compound of the present invention by a mammalian cell, particularly a human cell. Typically, the cell uptake of a compound of the present invention in the presence of a "transporter" is at least 50% higher than the cell uptake of the compound in the absence of the "transporter." Preferably, the cell uptake of a compound of the present invention in the presence of a "transporter" is at least 75% higher, preferably at least 100% or 200% higher, and more preferably at least 300%, 400% or 500% higher than the cell uptake of the compound in the absence of the "transporter." Methods of assaying cell uptake of a compound should be apparent to skilled artisans. For example, the compound to be delivered can be labeled with a radioactive isotope or another detectable marker (e.g., a fluorescence marker), and added to cultured cells in the presence or absence of a transporter, and incubated for a time period sufficient to allow maximal uptake. Cells can then be separated from the culture medium and the detectable signal (e.g., radioactivity) caused by the compound inside the cells can be measured. The result obtained in the presence of a transporter can be compared to that obtained in the absence of a transporter.

Many molecules and structures known in the art can be used as "transporter." In one embodiment, a penetratin is used as a transporter. For example, the homeodomain of Antennapedia, a *Drosophila* transcription factor, can be used as a transporter to deliver a compound of the present invention. Indeed, any suitable member of the penetratin class of peptides can be used to carry a compound of the present invention into cells. Penetratins are disclosed in, e.g., Derossi et al., *Trends Cell Biol.*, 8:84-87 (1998), which is incorporated herein by reference. Penetratins transport molecules attached thereto across cytoplasm membranes or nucleus membranes efficiently in a receptor-independent, energy-independent, and cell type-independent manner. Methods for using a penetratin as a carrier to deliver oligonucleotides and polypeptides are also disclosed in U.S. Pat. No. 6,080,724; Pooga et al., *Nat. Biotech.*, 16:857 (1998); and Schutze et al., *J. Immunol.*, 157:650 (1996), all of which are incorporated herein by reference. U.S. Pat. No. 6,080,724 defines the minimal requirements for a penetratin peptide as a peptide of 16 amino acids with 6 to 10 of which being hydrophobic. The amino acid at position 6 counting from either the N- or C-terminal is tryptophan, while the amino acids at positions 3 and 5 counting from either the N- or C-terminal are not both valine. Preferably, the helix 3 of the homeodomain of *Drosophila* Antennapedia is used as a transporter. More preferably, a peptide having a sequence of the amino acids 43-58 of the homeodomain Antp is employed as a transporter. In addition, other naturally occurring homologs of the helix 3 of the homeodomain of *Drosophila* Antennapedia can also be used. For example, homeodomains of Fushi-tarazu and Engrailed have been shown to be capable of transporting peptides into cells. See Han et al., *Mol. Cells*, 10:728-32 (2000). As used herein, the term "penetratin" also encompasses peptoid analogs of the penetratin peptides. Typically, the penetratin peptides and peptoid analogs thereof are covalently linked to a compound to be delivered into cells thus increasing the cellular uptake of the compound In another embodiment, the HIV-1 tat protein or a derivative thereof is used as a "transporter" covalently linked to a compound according to the present invention. The use of HIV-1 tat protein and derivatives thereof to deliver macromolecules into cells has been known in the art. See Green and Loewenstein, *Cell*, 55:1179 (1988); Frankel and Pabo, *Cell*, 55:1189 (1988); Vives et al., *J. Biol. Chem.*, 272:16010-16017 (1997); Schwarze et al., *Science*, 285:1569-1572 (1999). It is known that the sequence responsible for cellular uptake consists of the highly basic region, amino acid residues 49-57. See e.g., Vives et al., *J. Biol. Chem.*, 272:16010-16017 (1997); Wender et al., *Proc. Nat'l Acad. Sci. USA*, 97:13003-13008 (2000). The basic domain is believed to target the lipid bilayer component of cell membranes. It causes a covalently linked protein or nucleic acid to cross cell membrane rapidly in a cell type-independent manner. Proteins ranging in size from 15 to 120 kD have been delivered with this technology into a variety of cell types both in vitro and in vivo. See Schwarze et al., *Science*, 285:1569-1572 (1999). Any HIV tat-derived peptides or peptoid analogs thereof capable of transporting macromolecules such as peptides can be used for purposes of the present invention. For example, any native tat peptides having the highly basic region, amino acid residues 49-57 can be used as a transporter by covalently linking it to the compound to be delivered. In addition, various analogs of the tat peptide of amino acid residues 49-57 can also be useful transporters for purposes of this invention. Examples of various such analogs are disclosed in Wender et al., *Proc. Nat'l. Acad. Sci. USA*, 97:13003-13008 (2000) (which is incorporated herein by reference) including, e.g., d-Tat$_{49-57}$, retro-inverso isomers of l- or d-Tat$_{49-57}$ (i.e., l-Tat$_{57-49}$ and d-Tat$_{57-49}$), L-arginine oligomers, D-arginine oligomers, L-lysine oligomers, D-lysine oligomers, L-histine oligomers, D-histine oligomers, L-ornithine oligomers, D-ornithine oligomers, and various homologues, derivatives (e.g., modified forms with conjugates linked to the small peptides) and peptoid analogs thereof. Typically, arginine oligomers are preferred to the other oligomers, arginine oligomers are much more efficient in promoting cellular uptake. As used herein, the term "oligomer" means a molecule that includes a covalently linked chain of amino acid residues of the same amino acids having a large enough number of such amino acid residues to confer transporter activities on the molecule. Typically, an oligomer contains at least 6, preferably at least 7, 8, or at least 9 such amino acid residues. In one embodiment, the transporter is a peptide that includes at least six contiguous amino acid residues that are a combination of two or more of L-arginine, D-arginine, L-lysine, D-lysine, L-histidine, D-histine, L-ornithine, and D-ornithine.

Other useful transporters known in the art include, but are not limited to, short peptide sequences derived from fibroblast growth factor (See Lin et al., *J. Biol. Chem.*, 270:14255-14258 (1998)), Galparan (See Pooga et al., *FASEB J.* 12:67-77 (1998)), and HSV-1 structural protein VP22 (See Elliott and O'Hare, *Cell*, 88:223-233 (1997)).

As disclosed in the commonly assigned U.S. Provisional Application Ser. No. 60/276,259, the interaction between Tsg101 and HIV GAGp6 is essential for HIV viral budding. Disruption of the Tsg101-HIV GAGp6 interaction causes the host cells to display late-domain phenotype and, as a result, HIV viral budding is inhibited. Thus, in one embodiment, a compound capable of disrupting or interfering with the protein-protein interaction between the host cellular protein Tsg101 and HIV GAG is administered to a patient.

Any compounds capable of interfering with the protein-protein interaction between Tsg101 and HIV GAG may be used. This means useful compounds include those that interfere with, block, disrupt or destabilize the protein-protein interaction; block or interfere with the formation of a protein complex by Tsg101 and HIV Pr55 GAG or HIV GAGp6; or destabilize, disrupt or dissociate an existing protein complex comprising Tsg101 and HIV Pr55 GAG or HIV GAGp6. Such compounds can be selected by various screening assays known in the art. For example, test compounds may be screened in an in vitro assay to select interaction antagonists. A Tsg101-HIV GAGp6 protein complex can be contacted with a test compound and disruption or destabilization of the protein complex can be detected. For example, the presence or absence of the protein complex can be detected by an antibody selectively immunoreactive with the protein complex. Thus, after incubation of the protein complex with a test compound, immunoprecipitation assay can be conducted with the antibody. If the test compound disrupts the protein complex, then the amount of immunoprecipitated protein complex in this assay will be significantly less than that in a control assay in which the same protein complex is not contacted with the test compound. Various other detection methods may be suitable in the dissociation assay, as will be apparent to skilled artisan apprised of the present disclosure. In one embodiment, one of the interacting partner with a detectable marker fused thereto is fixed to a solid support. For example, a GST-GAGp6 fusion protein is attached to a solid support. Then the other interacting partner with a detectable marker fused thereto (e.g., a myc-tagged Tsg101 fragment containing the UEV domain) is contacted with the immobilized first interacting partner in the presence of one or more test compounds. If binding between the two interacting partners occurs, the myc-tagged Tsg101 fragment is also immobilized, which can be detected using an anti-myc antibody after the binding reaction mixture is washed to remove unbound myc-tagged Tsg101 fragment.

Alternatively, test compounds can also be screened in any in vivo assays to select compounds capable of interfering with the interaction between Tsg101 and HIV GAGp6. Any in vivo assays known in the art useful in selecting compounds capable of interfering with the stability of the protein complexes of the present invention may be used.

In a preferred embodiment, one of the yeast two-hybrid systems or their analogous or derivative forms is used. Examples of suitable two-hybrid systems known in the art include, but are not limited to, those disclosed in U.S. Pat. Nos. 5,283,173; 5,525,490; 5,585,245; 5,637,463; 5,695,941; 5,733,726; 5,776,689; 5,885,779; 5,905,025; 6,037,136; 6,057,101; 6,114,111; and Bartel and Fields, eds., *The Yeast Two-Hybrid System*, Oxford University Press, New York, N.Y., 1997, all of which are incorporated herein by reference.

Typically, in a classic transcription-based two-hybrid assay, two chimeric genes are prepared encoding two fusion proteins: one contains a transcription activation domain fused to an interacting protein member of a protein complex of the present invention or an interacting domain of the interacting protein member, while the other fusion protein includes a DNA binding domain fused to another interacting protein member of the protein complex or an interacting domain thereof.

In a screening assay for dissociators, Tsg101, a mutant form or a binding domain thereof, and HIV GAGp6, or a mutant form or a binding domain thereof, are used as test proteins expressed in the form of fusion proteins as described above for purposes of a two-hybrid assay. The fusion proteins are expressed in a host cell and allowed to interact with each other in the presence of one or more test compounds.

In a preferred embodiment, a counterselectable marker is used as a reporter such that a detectable signal (e.g., appearance of color or fluorescence, or cell survival) is present only when the test compound is capable of interfering with the interaction between the two test proteins. In this respect, the reporters used in various "reverse two-hybrid systems" known in the art may be employed. Reverse two-hybrid systems are disclosed in, e.g., U.S. Pat. Nos. 5,525,490; 5,733,726; 5,885,779; Vidal et al., *Proc. Natl. Acad. Sci. USA,* 93:10315-10320 (1996); and Vidal et al., *Proc. Natl. Acad. Sci. USA,* 93:10321-10326 (1996), all of which are incorporated herein by reference.

Examples of suitable counterselectable reporters useful in a yeast system include the URA3 gene (encoding orotidine-5'-decarboxylase, which converts 5-fluoroorotic acid (5-FOA) to the toxic metabolite 5-fluorouracil), the CAN1 gene (encoding arginine permease, which transports toxic arginine analog canavanine into yeast cells), the GAL1 gene (encoding galactokinase, which catalyzes the conversion of 2-deoxygalactose to toxic 2-deoxygalactose-1-phosphate), the LYS2 gene (encoding α-aminoadipate reductase, which renders yeast cells unable to grow on a medium containing α-aminoadipate as the sole nitrogen source), the MET15 gene (encoding O-acetylhomoserine sulfhydrylase, which confers on yeast cells sensitivity to methyl mercury), and the CYH2 gene (encoding $L_{29}$ ribosomal protein, which confers sensitivity to cycloheximide). In addition, any known cytotoxic agents including cytotoxic proteins such as the diphtheria toxin (DTA) catalytic domain can also be used as counterselectable reporters. See U.S. Pat. No. 5,733,726. DTA causes the ADP-ribosylation of elongation factor-2 and thus inhibits protein synthesis and causes cell death. Other examples of cytotoxic agents include ricin, Shiga toxin, and exotoxin A of *Pseudomonas aeruginosa.*

For example, when the URA3 gene is used as a counterselectable reporter gene, yeast cells containing a mutant URA3 gene can be used as host cells (Ura⁻Foa$^R$ phenotype) for the in vivo assay. Such cells lack URA3-encoded functional orotidine-5'-phsphate decarboxylase, an enzyme required for the biosynthesis of uracil. As a result, the cells are unable to grow on media lacking uracil. However, because of the absence of a wild-type orotidine-5'-phsphate decarboxylase, the yeast cells cannot convert non-toxic 5-fluoroorotic acid (5-FOA) to a toxic product, 5-fluorouracil. Thus, such yeast cells are resistant to 5-FOA and can grow on a medium containing 5-FOA. Therefore, for example, to screen for a compound capable of disrupting interaction between Tsg101 and HIV GAGp6, Tsg101 can be expressed as a fusion protein with a DNA-binding domain of a suitable transcription activator while HIV GAGp6 is expressed as a fusion protein with a transcription activation domain of a suitable transcription activator. In the host strain, the reporter URA3 gene may be operably linked to a promoter specifically responsive to the association of the transcription activation domain and the DNA-binding domain. After the fusion proteins are expressed in the Ura⁻Foa$^R$ yeast cells, an in vivo screening assay can be conducted in the presence of a test compound with the yeast cells being cultured on a medium containing uracil and 5-FOA. If the test compound does not disrupt the interaction between Tsg101 and HIV GAGp6, active URA3 gene product, i.e., orotidine-5'-decarboxylase, which converts 5-FOA to toxic 5-fluorouracil, is expressed. As a result, the yeast cells cannot grow. On the other hand, when the test compound disrupts the interaction between Tsg101 and HIV GAGp6, no active orotidine-5'-decarboxylase is produced in the host yeast cells. Consequently, the yeast cells will survive and grow on the 5-FOA-containing medium. Therefore, compounds capable of interfering with or dissociating the interaction between Tsg101 and HIV GAGp6 can thus be identified based on colony formation.

As will be apparent, the screening assay of the present invention can be applied in a format appropriate for large-scale screening. For example, combinatorial technologies can be employed to construct combinatorial libraries of small organic molecules or small peptides. See generally, e.g., Kenan et al., *Trends Biochem. Sc.,* 19:57-64 (1994); Gallop et al., *J. Med. Chem.,* 37:1233-1251 (1994); Gordon et al., *J. Med. Chem.,* 37:1385-1401 (1994); Ecker et al., *Biotechnology,* 13:351-360 (1995). Such combinatorial libraries of compounds can be applied to the screening assay of the present invention to isolate specific modulators of particular protein-protein interactions. In the case of random peptide libraries, the random peptides can be co-expressed with the fusion proteins of the present invention in host cells and assayed in vivo. See e.g., Yang et al., *Nucl. Acids Res.,* 23:1152-1156 (1995). Alternatively, they can be added to the culture medium for uptake by the host cells.

Conveniently, yeast mating is used in an in vivo screening assay. For example, haploid cells of a-mating type expressing one fusion protein as described above is mated with haploid cells of alpha-mating type expressing the other fusion protein. Upon mating, the diploid cells are spread on a suitable medium to form a lawn. Drops of test compounds can be deposited onto different areas of the lawn. After culturing the lawn for an appropriate period of time, drops containing a compound capable of modulating the interaction between the particular test proteins in the fusion proteins can be identified by stimulation or inhibition of growth in the vicinity of the drops.

The screening assays for selecting compounds capable of interfering with protein-protein interactions can also be fine-tuned by various techniques to adjust the thresholds or sensitivity of the positive and negative selections. Mutations can be introduced into the reporter proteins to adjust their activities. The uptake of test compounds by the host cells can also be adjusted. For example, yeast high uptake mutants such as the erg6 mutant strains can facilitate yeast uptake of the test compounds. See Gaber et al., *Mol. Cell. Biol.,* 9:3447-3456 (1989). Likewise, the uptake of the selection compounds such as 5-FOA, 2-deoxygalactose, cycloheximide, α-aminoadipate, and the like can also be fine-tuned.

Any test compounds may be screened in the screening assays of the present invention to select compounds capable of interfering with the interaction between Tsg101 and HIV GAGp6. The test compounds may include, by way of example, proteins (e.g., antibodies, small peptides, artificial or natural proteins), nucleic acids, and derivatives, mimetics and analogs thereof, and small organic molecules having a molecular weight of no greater than 10,000 daltons, more preferably less than 5,000 daltons. Preferably, the test compounds are provided in library formats known in the art, e.g., in chemically synthesized libraries, recombinant expression libraries (e.g., phage display libraries), and in vitro translation-based libraries (e.g., ribosome display libraries).

In preferred embodiments, the compound capable of interfering with the interaction between Tsg101 and HIV GAGp6 used in the methods of the present invention comprises an amino acid sequence motif of $PX_1X_2P$ and capable of binding the UEV domain of Tsg 101, wherein $X_1$ and $X_2$ are any amino acids. Preferably, $X_2$ is an amino acid other than arginine (R). The compound which comprises the amino acid sequence motif $PX_1X_2P$ and is capable of binding the UEV domain of Tsg 101 can be of any type of chemical compounds so long as the compound is capable of binding the UEV domain of Tsg101. For example, the compound can be a peptide, a modified peptide, an oligonucleotide-peptide hybrid (e.g., PNA), etc.

In one embodiment, in the compound comprising an amino acid sequence motif $PX_1X_2P$ and capable of binding the UEV domain of Tsg 101, $X_1$ is selected from the group consisting of threonine (T), serine (S), and isoleucine (I), and $X_2$ is not R. In another embodiment, the $X_2$ in the motif is alanine (A) or threonine (T). In a more preferred embodiment, the compound administered has the amino acid sequence motif of $PX_1X_2P$, wherein $X_1$ is selected from the group consisting of T, S, and I, and $X_2$ is A or T.

Thus, the compound can be a tetrapeptide having an amino acid sequence of $PX_1X_2P$, wherein $X_2$ is an amino acid other than arginine. In one embodiment, the tetrapeptide has an amino acid sequence of P(T/S/I)(A/T)P (SEQ ID NOs:1-6). In a preferred embodiment, the tetrapeptide has the sequence of PTAP (SEQ ID NO:1). In another preferred embodiment, the tetrapeptide has the sequence of PSAP (SEQ ID NO. 2).

The compound can also include a longer peptide comprising the amino acid sequence motif of $PX_1X_2P$ and capable of binding the UEV domain of Tsg 101. For example, the compound may include a peptide of 5, 6, 7, 8 or 9 amino acids, preferably 10, 11, 12, 13, 14, 15 or more amino acids.

In a preferred embodiment, the compound includes a peptide that contains a contiguous span of at least 5, 6, 7, 8 or 9 amino acids, preferably 10, 11, 12, 13, 14, 15 or more amino acids of a naturally occurring HIV Gag sequence. However, generally speaking, the contiguous span has less than 50, preferably less than 40, more preferably less than 30 amino acids. The contiguous span should span the HIV late domain motif which can be the P(T/S/I)(A/T)P (SEQ ID NOs:1-6) motif or a variation thereof. Preferably, the late domain motif in the contiguous span is the P(T/S)AP (SEQ ID NO:1 or SEQ ID NO:2) motif. In specific embodiments, the compound includes an amino acid sequence selected from the group of EPTAP (SEQ ID NO:7), EPSAP (SEQ ID NO:8), PTAPP (SEQ ID NO:9), PSAPP (SEQ ID NO:10), EPTAPP (SEQ ID NO:11), EPSAPP (SEQ ID NO:12), PEPTAP (SEQ ID NO:13), PEPSAP (SEQ ID NO:14), RPEPTAP (SEQ ID NO:15), RPEPSAP (SEQ ID NO:16), PEPTAPP (SEQ ID NO:17), PEPSAPP (SEQ ID NO:18), EPTAPPEE (SEQ ID NO:19), EPSAPPEE (SEQ ID NO:20), EPTAPPAE (SEQ ID NO:21), PEPTAPPEE (SEQ ID NO:22), PEPTAPPAE (SEQ ID NO:23), PEPSAPPEE (SEQ ID NO:24), RPEPTAPPEE (SEQ ID NO:25), RPEPSAPPEE (SEQ ID NO:26), RPEPTAPPAE (SEQ ID NO:27), RPEPSAPPAE (SEQ ID NO:28), LQSRPEPTAPPEE (SEQ ID NO:29), LQSRPEPSAPPEE (SEQ ID NO:30), LQSRPEPSAPPEES (SEQ ID NO:31), and LQSRPEPSAPPEES (SEQ ID NO:32).

In another embodiment, the $PX_1X_2P$ motif in the compound according to the present invention is within an amino acid sequence that is at least 70 percent, preferably at least 80 percent or 85 percent, more preferably at least 90 percent or 95 percent identical to a contiguous span of at least 5, 6, 7, 8 or 9 amino acids, preferably 10, 11, 12, 13, 14, 15 or more amino acids, but preferably less than 50 or 40, more preferably less than 30 amino acids, of a naturally occurring HIV Gag sequence, which contiguous span of amino acids spans the HIV late domain motif. In this respect, the percentage identity is determined by the algorithm of Karlin and Altschul, *Proc. Natl. Acad. Sci. USA,* 90:5873-77 (1993), which is incorporated into the various BLAST programs. Specifically, the percentage identity is determined by the "BLAST 2 Sequences" tool, which is available at the National Center for Biotechnology Information website. See Tatusova and Madden, *FEMS Microbiol. Lett.,* 174(2):247-50 (1999). For pairwise protein-protein sequence comparison, the BLASTP 2.1.2 program is employed using default parameters (Matrix: BLOSUM62; gap open: 11; gap extension: 1; x_dropoff: 15; expect: 10.0; and wordsize: 3, with filter). It should be understood that such homologue peptides should retain the ability to bind the UEV domain of Tsg101. Preferably, in this embodiment of the present invention, $X_1$ in the $PX_1X_2P$ motif is selected from the group consisting of T, S, and I, and $X_2$ is not R. More preferably, $X_1$ is selected from the group consisting of T, S, and I, and $X_2$ is A or T. Most preferably, $X_1$ is T or S, and $X_2$ is A.

The homologues can be made by site-directed mutagenesis based on a late domain motif-containing HIV Pr55 GAG polyprotein sequence of HIV or other lentiviruses. The site-directed mutagenesis can be designed to generate amino acid substitutions, insertions, or deletions. Methods for conducting such mutagenesis should be apparent to skilled artisans in the field of molecular biology. The resultant homologues can be tested for their binding affinity to the UEV domain of Tsg101.

The peptide portion in the compounds according to the present invention can also be in a modified form. Various modifications may be made to improve the stability and solubility of the compound, and/or optimize its binding affinity to the UEV domain of Tsg101. Examples of modified forms include, but are not limited to, glycosylated forms, phosphorylated forms, myristoylated forms, palmitoylated forms, ribosylated forms, acetylated forms, etc. Modifications also include intra-molecular crosslinking and covalent attachment to various moieties such as lipids, flavin, biotin, polyethylene glycol or derivatives thereof, etc. In addition, modifications may also include cyclization, and branching. Amino acids other than the conventional twenty amino acids encoded by genes may also be included in a polypeptide sequence in the compound of the present invention. For example, the compounds may include D-amino acids in place of L-amino acids.

To increase the stability of the peptidic compounds according to the present invention, various protection groups can also be incorporated into the amino acid residues of the compounds. In particular, terminal residues are preferably protected. Carboxyl groups may be protected by esters (e.g., methyl, ethyl, benzyl, p-nitrobenzyl, t-butyl or t-amyl esters, etc.), lower alkoxyl groups (e.g., methoxy, ethoxy, propoxy, butoxy, etc.), aralkyloxy groups (e.g., benzyloxy, etc.), amino groups, lower alkylamino or di(lower alkyl)amino groups. The term "lower alkoxy" is intended to mean an alkoxy group having a straight, branched or cyclic hydrocarbon moiety of up to six carbon atoms. Protection groups for amino groups may include lower alkyl, benzyloxycarbonyl, t-butoxycarbonyl, and sobornyloxycarbonyl. "Lower alkoxy" is intended to mean an alkyl group having a straight, branched or cyclic hydrocarbon moiety of up to six carbon atoms. In one example, a 5-oxo-L-prolyl residue may be used in place of a prolyl residue. A 5-oxo-L-prolyl residue is especially desirable at the N-terminus of a peptide compound. In another example, when a proline residue is at the C-terminus of a peptide compound, a N-ethyl-L-prolinamide residue may be desirable in place of the proline residue. Various other protection groups known in the art useful in increasing the stability of peptide compounds can also be employed.

Additionally, as will be apparent to skilled artisans apprised of the present disclosure, peptide mimetics can be designed based on the above-described $PX_1X_2P$ motif-containing compounds according to the present invention. However, it is noted that the mimetics must be capable of binding the UEV domain of Tsg 101. For example, peptoid analogs of the P(T/S)(A/T)P (SEQ ID NOs:1-4) motif can be prepared using known methods. Peptoids are oligomeric N-substituted glycines. Typically, various side chain groups can be included when forming an N-substituted glycine (peptoid monomer)

that mimics a particular amino acid. Peptoid monomers can be linked together to form an oligomeric N-substituted glycines—peptoid. Peptoids are easy to synthesize in large amounts. In contrast to peptides, the backbone linkage of peptoids are resistant to hydrolytic enzymes. In addition, since a variety of functional groups can be presented as side chains off of the oligomeric backbone, peptoid analogs corresponding to any peptides can be produced with improved characterics. See Simon et al., *Proc. Natl. Acad. Sci. USA*, 89:9367-9371 (1992); Figliozzi et al., *Methods Enzymol.*, 267:437-447 (1996); Horwell, *Trends Biotechnol.*, 13:132-134 (1995); and Horwell, *Drug Des. Discov.*, 12:63-75 (1994), all of which are incorporated herein by reference.

Thus, peptoid analogs of the above-described $PX_1X_2P$ motif-containing compounds of the present invention can be made using methods known in the art. The prepared peptoid analogs can be tested for their binding affinity to Tsg101. They can also be tested in anti-viral assays for their ability to inhibit lentivirus budding from infected host cells and ability to inhibit lentivirus propagation. In particular, they can be tested for ability to suppress HIV budding from infected human cells and inhibit HIV propagation.

Mimetics of the compounds of the present invention can also be selected by rational drug design and/or virtual screening. Methods known in the art for rational drug design can be used in the present invention. See, e.g., Hodgson et al., *Bio/Technology,* 9:19-21 (1991); U.S. Pat. Nos. 5,800,998 and 5,891,628, all of which are incorporated herein by reference. An example of rational drug design is the development of HIV protease inhibitors. See Erickson et al., *Science,* 249: 527-533 (1990). Structural information on the UEV domain of Tsg101 and/or the binding complex formed by the Tsg101 UEV domain and the HIV Gag p6 PTAP (SEQ ID NO:1) motif are obtained. The interacting complex can be studied using various biophysics techniques including, e.g., X-ray crystallography, NMR, computer modeling, mass spectrometry, and the like. Likewise, structural information can also be obtained from protein complexes formed by the Tsg101 UEV domain and a variation of the PTAP (SEQ ID NO:1) motif.

Computer programs are employed to select compounds based on structural models of the binding complex formed by the Tsg101 UEV domain and the HIV Gag p6 PTAP (SEQ ID NO:1) motif. In addition, once an effective compound is identified, structural analogs or mimetics thereof can be produced based on rational drug design with the aim of improving drug efficacy and stability, and reducing side effects.

In addition, understanding of the interaction between the Tsg101 UEV domain and compounds of the present invention can also be derived from mutagenesis analysis using yeast two-hybrid system or other methods for detection protein-protein interaction. In this respect, various mutations can be introduced into the interacting proteins and the effect of the mutations on protein-protein interaction is examined by a suitable method such as in vitro binding assay or the yeast two-hybrid system.

Various mutations including amino acid substitutions, deletions and insertions can be introduced into the protein sequence of the Tsg101 UEV domain and/or a compound of the present invention using conventional recombinant DNA technologies. Generally, it is particularly desirable to decipher the protein binding sites. Thus, it is important that the mutations introduced only affect protein-protein interaction and cause minimal structural disturbances. Mutations are preferably designed based on knowledge of the three-dimensional structure of the interacting proteins. Preferably, mutations are introduced to alter charged amino acids or hydrophobic amino acids exposed on the surface of the proteins, since ionic interactions and hydrophobic interactions are often involved in protein-protein interactions. Alternatively, the "alanine scanning mutagenesis" technique is used. See Wells, et al., *Methods Enzymol.,* 202:301-306 (1991); Bass et al., *Proc. Natl. Acad. Sci. USA,* 88:4498-4502 (1991); Bennet et al., *J. Biol. Chem.,* 266:5191-5201 (1991); Diamond et al., *J. Virol.,* 68:863-876 (1994). Using this technique, charged or hydrophobic amino acid residues of the interacting proteins are replaced by alanine, and the effect on the interaction between the proteins is analyzed using e.g., an in vitro binding assay. In this manner, the domains or residues of the proteins important to compound-target interaction can be identified.

Based on the structural information obtained, structural relationships between the Tsg101 UEV domain and a compound of the present invention are elucidated. The moieties and the three-dimensional structures critical to the interaction are revealed. Medicinal chemists can then design analog compounds having similar moieties and structures.

The residues or domains critical to the modulating effect of the identified compound constitute the active region of the compound known as its "pharmacophore."

Once the pharmacophore has been elucidated, a structural model can be established by a modeling process that may incorporate data from NMR analysis, X-ray diffraction data, alanine scanning, spectroscopic techniques and the like. Various techniques including computational analysis, similarity mapping and the like can all be used in this modeling process. See e.g., Perry et al., *in OSAR: Quantitative Structure-Activity Relationships in Drug Design*, pp. 189-193, Alan R. Liss, Inc., 1989; Rotivinen et al., *Acta Pharmaceutical Fennica,* 97:159-166 (1988); Lewis et al., *Proc. R. Soc. Lond.,* 236: 125-140 (1989); McKinaly et al., *Annu. Rev. Pharmacol. Toxiciol.,* 29:111-122 (1989). Commercial molecular modeling systems available from Polygen Corporation, Waltham, Mass., include the CHARMm program, which performs the energy minimization and molecular dynamics functions, and QUANTA program which performs the construction, graphic modeling and analysis of molecular structure. Such programs allow interactive construction, visualization and modification of molecules. Other computer modeling programs are also available from BioDesign, Inc. (Pasadena, Calif.), Hypercube, Inc. (Cambridge, Ontario), and Allelix, Inc. (Mississauga, Ontario, Canada).

A template can be formed based on the established model. Various compounds can then be designed by linking various chemical groups or moieties to the template. Various moieties of the template can also be replaced. These rationally designed compounds are further tested. In this manner, pharmacologically acceptable and stable compounds with improved efficacy and reduced side effect can be developed. The compounds identified in accordance with the present invention can be incorporated into a pharmaceutical formulation suitable for administration to an individual.

The mimetics including peptoid analogs can exhibit optimal binding affinity to the UEV domain of human Tsg101 or animal orthologs thereof. Various known methods can be utilized to test the Tsg101-binding characteristics of a mimetics. For example, the entire Tsg101 protein or a fragment thereof containing the UEV domain may be recombinantly expressed, purified, and contacted with the mimetics to be tested. Binding can be determined using a surface plasmon resonance biosensor. See e.g., Panayotou et al., *Mol. Cell. Biol.,* 13:3567-3576 (1993). Other methods known in the art for estimating and determining binding constants in protein-protein interactions can also be employed. See Phizicky and Fields, et al., *Microbiol. Rev.,* 59:94-123 (1995). For example, protein affinity chromatography may be used. First, columns are prepared with different concentrations of an interacting member, which is covalently bound to the columns. Then a preparation of its interacting partner is run through the column and washed with buffer. The interacting partner bound to the interacting member linked to the column is then eluted. Binding constant is then estimated based on the concentrations of the bound protein and the eluted protein. Alternatively, the method of sedimentation through gradients monitors the rate of sedimentation of a mixture of proteins through gradients of glycerol or sucrose. At concentrations above the binding constant, the two interacting members sediment as a complex. Thus, binding constant can be calculated based on the concentrations. Other suitable methods known in the art for estimating binding constant include but are not limited to gel filtration column such as nonequilibrium "small-zone" gel filtration columns (See e.g., Gill et al., *J. Mol. Biol.*, 220:307-324 (1991)), the Hummel-Dreyer method of equilibrium gel filtration (See e.g., Hummel and Dreyer, *Biochim. Biophys. Acta*, 63:530-532 (1962)) and large-zone equilibrium gel filtration (See e.g., Gilbert and Kellett, *J. Biol. Chem.*, 246:6079-6086 (1971)), sedimentation equilibrium (See e.g., Rivas and Minton, *Trends Biochem.*, 18:284-287 (1993)), fluorescence methods such as fluorescence spectrum (See e.g., Otto-Bruc et al, *Biochemistry*, 32:8632-8645 (1993)) and fluorescence polarization or anisotropy with tagged molecules (See e.g., Weiel and Hershey, *Biochemistry*, 20:5859-5865 (1981)), and solution equilibrium measured with immobilized binding protein (See e.g., Nelson and Long, *Biochemistry*, 30:2384-2390 (1991)).

The compounds capable of interfering with the interaction between Tsg101 and HIV GAGp6 can be delivered into cells by direct cell internalization, receptor mediated endocytosis, or via a "transporter." It is noted that a compound preferably is delivered into patient's cells in order to achieve optimal results. Preferably, peptidic transporters as described above such as penetratins and HIV tat protein are employed. Fusion proteins can be conveniently made by recombinant expression to contain a transporter peptide covalently linked by a peptide bond to a peptide having the $PX_1X_2P$ motif. Alternatively, conventional methods can be used to chemically synthesize a transporter peptide or a peptide of the present invention or both.

In accordance with another aspect of the present invention, a method for treating and/or preventing HIV infection and AIDS is provided comprising administering to a patient in need of treatment cells displaying HIV late-domain phenotype. That is, cells displaying HIV late-domain phenotype are prepared in vitro and delivered to a patient in need of treatment. Although cells from a variety of sources may be employed to prepare cells displaying HIV late-domain phenotype, mammalian cells including human cells and others may be preferable.

As will be apparent to skilled artisans, the methods described above for causing, in the body, the formation of cells displaying HIV late-domain phenotype can be used in in vitro procedures to create cells displaying HIV late-domain phenotype. For example, a mutant HIV Pr55 GAG polypeptide sufficient for viral particle assembly but devoid of the P(T/S)AP (SEQ ID NO:1 or SEQ ID NO:2) motif in the GAGp6 domain or devoid of the entire GAGp6 domain may be introduced into cells in vitro to initiate the assembly of virus-like particle and form cells displaying HIV late-domain phenotype. Alternatively, a nucleic acid encoding a mutant HIV Pr55 GAG polypeptide sufficient for virus-like particle assembly but devoid of the P(T/S)AP (SEQ ID NO:1 or SEQ ID NO:2) motif in the GAGp6 domain or devoid of the entire GAGp6 domain is introduced into cells in vitro to express the mutant HIV Pr55 GAG polypeptide in the cells.

In another embodiment, a wild-type or mutant HIV Pr55 GAG polypeptide sufficient for viral particle assembly or a nucleic acid encoding such a polypeptide can be administered to cells defective in respect to one or more proteins required for HIV budding. For example, human cells with the Tsg101 gene being knocked out may be used for this purpose. Also, dominant-negative mutations in the Vps4 gene will also prevent HIV budding from the cells and cause late-domain phenotype when a wild-type or mutant HIV Pr55 GAG polypeptide sufficient for viral particle assembly is produced in the cells. Methods for creating Tsg101-deficient cells or cells with dominant-negative mutations in the Vps4 gene should be apparent to skilled artisans.

A nucleic acid encoding a wild-type or mutant HIV Pr55 GAG polypeptide or vectors containing the nucleic acid can be introduced into cells in vitro using any known techniques such as calcium phosphate precipitation, microinjection, lipofection, electroporation, gene gun, receptor-mediated endocytosis, and the like. The wild-type or mutant HIV Pr55 GAG polypeptide can be introduced into cells in vitro by attaching the polypeptide to a transporter as described above capable of increasing the cell uptake of the polypeptide. The cells displaying or capable of displaying HIV late-domain phenotype can be administered to a patient by, e.g., injection or cell transplantation. The appropriate amount of cells delivered to a patient will vary with patient conditions, and desired effect, which can be determined by a skilled artisan. See e.g., U.S. Pat. Nos. 6,054,288; 6,048,524; and 6,048,729.

3. Adjuvants

Although not required, it is preferred that an adjuvant capable of stimulating immune response is also administered to a patient who is treated with cells displaying HIV late domain phenotype or with a compound (nucleic acids, polypeptides or small organic compounds) capable of causing the formation, in a patient's body, of cells displaying HIV late domain phenotype. As used herein, the term "adjuvant" means any substance that is not a component of HIV but is capable of stimulating or enhancing immune responses to an immunogen administered to a patient.

As disclosed in the commonly assigned U.S. Provisional Application Ser. No. 60/276,259, the disruption or interference with the protein-protein interaction between the host cellular protein Tsg101 and HIV GAG can in itself be effective in treating and/or prevent HIV infection and AIDS by way of inhibiting HIV viral budding and propagation. However, the disruption or interference with the protein-protein interaction between the host cellular protein Tsg101 and HIV GAG also causes the formation of cells displaying HIV late-domain phenotype which act as immunogens in eliciting immune responses in the patient. Therefore, the compounds administered to a patient capable of disrupting or interfering with the protein-protein interaction between Tsg101 and HIV GAG can also stimulate immune responses in the patient against HIV viruses, particularly cytotoxic T lymphocytes (CTL) response. In this respect, the administration of an adjuvant capable of enhancing the patient's immune response, particularly cytotoxic T lymphocytes (CTL) response, along with the administration to the patient of a compound capable of disrupting or interfering with the protein-protein interaction between Tsg101 and HIV GAGp6 will significantly bolster the anti-HIV immune response in the patient and result in a treatment efficacy significantly greater than the administration of the compound alone.

Similarly, an adjuvant capable of enhancing patient immune response, particularly CTL response, would also significantly boost the prophylactic and/or therapeutic effect when coupled with a mutant HIV Pr55 GAG polypeptide that is sufficient for viral particle assembly but causes late-domain phenotype in cells, or a nucleic acid encoding the mutant HIV Pr55 GAG polypeptide, or with cells displaying HIV late-domain phenotype.

Any pharmaceutically acceptable adjuvant may be used so long as the adjuvant is capable of stimulating immune response against cells displaying HIV late-domain phenotype or against the HIV viral proteins in such cells, and thus can enhance immune response against HIV viruses in a patient. For example, alum has long been used as an adjuvant for human use. Another example of suitable adjuvant is MF59. See Minutello et al., *Vaccine,* 17:99-104 (1999). Another useful adjuvant in development that may also be used is LTR72, a mutant of *E. coli* heat-labile enterotoxin with partial knockout of ADP-ribosyltransferase activity. See Giuliani et al., *J. Exp. Med.,* 187:1123-1132 (1998). Polyphosphazine adjuvant may also be used. In addition, cytokines and lymphokines may also be used as adjuvants along with the cells, polypeptides, nucleic acids and/or a compound capable of disrupting or interfering with the protein-protein interaction between Tsg101 and HIV GAG. Examples of cytokines and lymphokines include, but are not limited to, interleukins such as IL-1, IL-2, IL-4, IL-6, IL-8, IL-10 and IL-12, interferons such as alpha-interferon and gamma-interferon, tumor necrosis factor (TNF), platelet derived growth factor (PDGF), GCSF, granulocyte-macrophage colony-stimulating factor (GM-CSF), epidermal growth factor (EGF), and the like.

Preferably, adjuvants capable of stimulating cellular immune responses, particularly cytotoxic T lymphocytes (CTL) responses, are used. A synergistic effect on the induction of HIV-specific CTL response can be achieved when adjuvants capable of stimulating CTL response are used in the presence of cells displaying HIV late-domain phenotype. This is especially beneficial to the prevention and treatment of HIV infection and AIDS because it is now known that a potent killer T cell response to HIV is critical to effective inhibition of HIV in humans.

Many adjuvants capable of stimulating cellular immune responses are known in the art. For example, cytokines secreted by helper T cells called Th1 cells have been shown to promote cellular responses. Such Th1 type cytokines include interleukin-2 (IL-2), interleukin-4, and interleukin-12 (IL-12), interleukin-18, among others. In addition, fusion proteins having one of such Th1 type cytokines (e.g., IL-2) may also be used. For example, the fusion proteins may include a cytokine and the Fc portion of immunoglobulin G (IgG). See e.g., Barouch et al., *Science,* 290:486-492 (2000), which is incorporated herein by reference. Other preferred adjuvants capable of stimulating cell-mediated immune responses include interferons such as alpha-interferon, beta-interferon and gamma-interferon. Certain chemokines may also be used to enhance cellular immune responses. Such chemokines are small molecules that attract T cells to infected tissues. Additionally, certain short bacterial immunostimulatory DNA sequences (ISSs) have also been discovered as CTL response-promoting adjuvants that potently stimulate immune responses to co-administered antigens. See Roman et al., *Nat. Med.,* 3:849-854 (1997), which is incorporated herein by reference. Thus, noncoding, ISS-enriched plasmid DNAs or ISS oligonucleotides (ISS-ODNs) can also be used in the present invention as adjuvants to enhance cellular immunity against cells displaying HIV late-domain phenotype.

One or more adjuvants can be used for purposes of the present invention. The adjuvant(s) can be administered in the same composition as the cells or compounds as described above. Alternatively, the adjuvant(s) can also be given to a patient separately. Accordingly, the present invention also provides compositions comprising cells displaying HIV late-domain phenotype and one or more adjuvants capable of enhancing immune responses in a patient. In a preferred embodiment, the compositions include cells displaying HIV late-domain phenotype and one or more adjuvants capable of enhancing cellular immune response, cell-mediated immune response or CTL response.

As is apparent from the above description, many of the suitable adjuvants are proteins or peptides. Such adjuvants can be administered to patients in the form of nucleic acids (e.g., DNA, RNA, and the like) so long as the administered nucleic acids are capable of expressing the adjuvants they encode. Thus, the term "administering an adjuvant to a patient" or a paraphrase thereof also encompasses administering a nucleic acid encoding a protein adjuvant and capable of expressing the adjuvant in a patient's body. Methods for administering nucleic acids are described above.

Accordingly, The present invention provides a composition comprising at least (1) a mutant HIV Pr55 GAG polypeptide sufficient for viral particle assembly but devoid of late domain motifs, or a nucleic acid encoding the same, and (2) an adjuvant capable of stimulating cytotoxic T lymphocyte (CTL) response, or a nucleic acid encoding a proteinaceous adjuvant. The two nucleic acids can be incorporated into separate expression vectors. Preferably, the two nucleic acids are carried within the same expression vector. In one embodiment, each of the two nucleic acids is operably linked to a transcriptional promoter, which drives the transcription from the nucleic acid linked to the promoter. In preferred embodiments, the nucleic acid encoding a mutant HIV Pr55 GAG polypeptide sufficient for viral particle assembly but devoid of late domain motifs is capable of expressing the mutant HIV Pr55 GAG polypeptide in the absence of HIV Rev protein. For example, the nucleic acid may contain one or more mutations that decrease the effect of an inhibitory/instability sequence that is present in the corresponding nucleotide sequence of the native HIV GAG nucleic acid. Methods for making the expression vectors and compositions and for administering them to a patient are as described elsewhere in the present disclosure.

4. Combination Therapy

The methods and compositions according to the present invention are distinct from other known or commercially available approaches for treating or preventing HIV infection and AIDS. Therefore, it may be desirable to employ combination therapies to combine a method of the present invention with other prophylactic or treatment methods so as to increase the prophylactic or therapeutic effect.

Thus, any other methods useful in treating or preventing HIV infection and AIDS may be combined with the methods of the present invention. The therapeutic and/or prophylactic materials in the methods of the present invention and in other methods may be combined in the same pharmaceutical composition or administered separately. In addition, one or more adjuvants described above may be included in the same composition or administered separately in the combination therapy approaches. However, it is to be understood that such other anti-HIV agents should be pharmaceutically compatible with the cells, nucleic acids, polypeptides or other active agents, and/or adjuvants of the present invention. By "pharmaceutically compatible" it is intended that the other antiviral agent(s) will not interact or react with the cells, nucleic acids, polypeptides or other active agents, and/or adjuvants of the present invention, directly or indirectly, in such a way as to substantially adversely affect the effect of the treatment, or to cause any significant adverse side reaction in the patient.

In one embodiment, an HIV protein or a nucleic acid encoding an HIV protein is administered in the combination therapy. In specific embodiments, an HIV surface protein, e.g., an envelope protein, or a nucleic acid encoding the HIV protein is administered in the combination therapy. The envelope protein can be selected from any HIV strains or clades, and can be gp41, gp120, gp160 or any other forms. An envelope protein can be injected directly into a patient to elicit antibodies against the envelope protein. The nucleic acid can be administered as a genetic vaccine in a plasmid as described above. Alternatively, the nucleic acid is incorporated into a live vector including, e.g., recombinant viral vector (e.g., vaccinia vector, canarypox vector, polio virus vector, Semliki forest virus vector, Venezuelan equine encephalitis virus vector, etc.), recombinant bacterial vector, and the like, as described above. Other HIV proteins or nucleic acids encoding such other HIV proteins may also be employed in a similar manner. Such other HIV proteins include, but are not limited to, gag polypeptide, POL, protease, Nef, Vpr, Vpu, Tat1, Tat2, reverse transcriptase, integrase, Vif, etc.

In another embodiment, an inactivated whole HIV virus is used in the combination therapy of the present invention. For example, U.S. Pat. No. 5,698,432 (which is incorporated herein by reference) discloses an inactivated HIV virus useful as an HIV vaccine. The inactivated virus is produced by treating a virus with a general inactivating agent, deaggregating the virus with a suitable solvent or detergent, treating the virus with an RNA inactivating agent, and stabilizing the virus with a cross-linking agent. U.S. Pat. No. 6,017,543 (which is incorporated herein by reference) describes treated HIV viruses free of outer-envelope, which can be used as HIV vaccines.

In yet another embodiment, HIV virus-like particles are used in the combination therapy of the present invention. For example, U.S. Pat. Nos. 5,439,809 and 5,985,641 (both of which are incorporated herein by reference) disclose non-infectious immunogenic HIV particles useful as HIV vaccines. The virus-like particles are produced by expressing, in mammalian cells, a genetically modified HIV genome devoid of long terminal repeats.

In addition, various anti-viral compounds known in the art may also be included in the combination therapy according to the present invention. Compounds suitable for use in combination therapies with the cells, nucleic acids, polypeptides and other active agents according to the present invention, in the presence or absence of one or more adjuvants described above, include, but are not limited to, HIV protease inhibitors, nucleoside HIV reverse transcriptase inhibitors, non-nucleoside HIV reverse transcriptase inhibitors, and HIV integrase inhibitors.

Examples of nucleoside HIV reverse transcriptase inhibitors include 3'-Azido-3'-deoxythymidine (Zidovudine, also known as AZT and RETROVIR®), 2',3'-Didehydro-3'-deoxythymidine (Stavudine, also known as 2',3'-dihydro-3'-deoxythymidine, d4T, and ZERIT®), (2R-cis)-4-Amino-1-[2-(hydroxymethyl)-1,3-oxathiolan-5-yl]-2(1H)-pyrimidinone (Lamivudine, also known as 3TC, and EPIVIR®), and 2',3'-dideoxyinosine (ddI).

Examples of non-nucleoside HIV reverse transcriptase inhibitors include (−)-6-Chloro-4-cyclopropylethynyl-4-trifluoromethyl-1,4-dihydro-2H-3,1-benzoxazin-2-one (efavirenz, also known as DMP-266 or SUSTIVA®) (see U.S. Pat. No. 5,519,021), 1-[3-[(1-methylethyl)amino]-2-pyridinyl]-4-[[5-[(methylsulfonyl)amino]-1H-indol-2-yl]carbonyl]piperazine (Delavirdine, see PCT International Patent Application No. WO 91/09849), and (1S,4R)-cis-4-[2-amino-6-(cycloprpoylamino)-9H-purin-9-yl]-2-cyclopentene-1-methanol (Abacavir).

Examples of protease inhibitors include [5S-(5R*,8R*,10R*,11R*)]-10-hydroxy-2-methyl-5-(1-methylethyl)-1-[2-(1-methylethyl)-4-thiazolyl]-3,6-dioxo-8,11-bis(phenylmethyl)-2,4,7,12-tetraazamidecan-13-oic acid 5-thiazolylmethyl ester (Ritonavir, marketed by Abbott as NORVIR®), [3S-[2(2S*,3S*),3a,4ab,8ab]]-N-(1,1-dimethylethyl)decahydro-2-[2-hydroxy-3-[(3-hydroxy-2-methylbenzoyl)amino]-4-(phenylthio)butyl]-3-isoquinolinecarboxamide monomethanesulfonate (Nelfinavir, marketed by Agouron as VIRACEPT®), N-(2(R)-hydroxy-1(S)-indanyl)-2(R)-phenylmethyl-4-(S)-hydroxy-5-(1-(4-(2-benzo[b]furanylmethyl)-2(S)-N'(t-butylcarboxamido)-piperazinyl))-pentaneamide (See U.S. Pat. No. 5,646,148), N-(2(R)-hydroxy-1(S)-indanyl)2(R)-phenylmethyl-4-(S)-hydroxy-5-(1-(4-(3-pyridylmethyl)-2(S)-N'-(t-butylcarboxamido)-piperazinyl))-pentaneamide (Indinavir, marketed by Merck as CRIXIVAN®), 4-amino-N-((2 syn,3S)-2-hydroxy-4-phenyl-3-((S)-tetrahydrofuran-3-yloxycarbonylamino)-butyl)-N-isobutyl-benzenesulfonamide (amprenavir, see U.S. Pat. No. 5,585,397), and N-tert-butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide (Saquinavir, marketed by Roche Laboratories as INVIRASE®).

Examples of suitable HIV integrase inhibitors are disclosed in U.S. Pat. Nos. 6,110,716; 6,124,327; and 6,245,806, which are incorporated herein by reference.

In addition, antifusogenic peptides disclosed in, e.g., U.S. Pat. No. 6,017,536 can also be included in the combination therapies according to the present invention. Such peptides typically consist of a 16 to 39 amino acid region of a simian immunodeficiency virus (SIV) protein and are identified through computer algorithms capable of recognizing the ALLMOTI5, 107x178x4, or PLZIP amino acid motifs. See U.S. Pat. No. 6,017,536, which is incorporated herein by reference.

In the combination therapies, the active agents provided according to the present invention as described in Sections 1-3 and the other anti-HIV agents can be administered in the same pharmaceutical composition or administered separately. Thus, the present invention also encompasses compositions containing one or more active agents provided according to the present invention as described in Sections 1-3 as well as one or more other anti-HIV agents known in the art as described above.

5. Dosage, Formulation and Administration

Typically, the active agents (cells, polypeptides, small organic molecules, nucleic acids in plasmid vectors or recombinant vectors) of the present invention are administered to a patient in a pharmaceutical composition, which typically includes one or more pharmaceutically acceptable carriers that are inherently nontoxic and non-therapeutic.

The pharmaceutical composition according to the present invention may be administered to a subject needing treatment or prevention through any appropriate routes such as parenteral, oral, mucosal or topical administration. The active agents of this invention are administered at a therapeutically or prophylactically effective amount to achieve the desired therapeutic and/or prophylactic effect without causing any serious adverse effects in the patient treated. Generally, the toxicity profile and therapeutic or prophylactic efficacy of the active agents can be determined by standard pharmaceutical procedures in suitable cell models or animal models or human clinical trials. As is known in the art, the $LD_{50}$ represents the dose lethal to about 50% of a tested population. The $ED_{50}$ is a parameter indicating the dose therapeutically or prophylactically effective in about 50% of a tested population. Both $LD_{50}$ and $ED_{50}$ can be determined in cell models and animal models. In addition, the $IC_{50}$ may also be obtained in cell models and animal models, which stands for the circulating plasma concentration that is effective in achieving about 50% of the maximal inhibition of the symptoms of a disease or disorder. Such data may be used in designing a dosage range for clinical trials in humans. Typically, as will be apparent to skilled artisans, the dosage range for human use should be designed such that the range centers around the $ED_{50}$ and/or $IC_{50}$, but significantly below the $LD_{50}$ obtained from cell or animal models.

Typically, the cells displaying HIV late-domain phenotype may be effective at an amount of from about 10 cells to about $20 \times 10^6$ cells per dosage with an administration frequency of once per year, once per month up to once per day. The cells can be injected in a composition having a suitable pharmaceutically acceptable carrier. For example, such a composition may include cells suspended in a standard sterile cell culture medium, preferably devoid of serum. Alternatively, the cells may be simply suspended in a saline solution, e.g., PBS, or other standard cell transplantation carrier before administration. Typically, the composition should contain one or more agents for maintaining optimal isotonicity, isomocity and pH. Suitable adjuvant(s) may also be included in the composition. The cell-containing composition can be administered to a patient through any suitable routes, e.g., by parenteral injection or transplantation. Preferably, the cells are injected intravenously.

When a nucleic acid (either alone or in a plasmid vector or a recombinant live vector) is used as an active agent in the present invention, the nucleic acid can be administered in an amount of from about 0.1 microgram to about 5000 milligram, preferably from about 1 microgram to about 500 milligram per dosage. The appropriate amount can be administered daily, weekly, monthly, bimonthly, semi-annually or annually. The nucleic acid can be administered to a patient in a manner as described above in Section 1 or by a standard procedure known in the art, as will be apparent to skilled artisans.

Typically, the mutant HIV Pr55 GAG polypeptides and the other active peptidic or small organic compounds of the present invention capable of causing the formation of cells displaying HIV late-domain phenotype can be effective at an amount of from about 0.01 microgram to about 10,000 mg per day, preferably from about 1 microgram to about 2500 mg per day. However, the amount can vary with the body weight of the patient treated and the state of disease conditions. The active ingredient may be administered at once, or may be divided into a number of smaller doses to be administered at predetermined intervals of time. The suitable dosage unit for each administration of the compounds of the present invention can be, e.g., from about 0.01 microgram to about 2000 mg, preferably from about 1 microgram to about 1000 mg.

In the case of combination therapy, a therapeutically or prophylactically effective amount of another anti-HIV compound can be administered in a separate pharmaceutical composition, or alternatively included in the pharmaceutical composition that contains a compound according to the present invention. The pharmacology and toxicology of many of such other anti-HIV compounds are known in the art. See e.g., Physicians Desk Reference, Medical Economics, Montvale, N.J.; and The Merck Index, Merck & Co., Rahway, N.J. The therapeutically or prophylactically effective amounts and suitable unit dosage ranges and route of administration of such compounds used in art can be equally applicable in the present invention.

It should be understood that the dosage ranges set forth above are exemplary only and are not intended to limit the scope of this invention. The therapeutically or prophylactically effective amount for each active agent can vary with factors including but not limited to the activity of the agent used, stability of the active agent in the patient's body, the severity of the conditions to be alleviated, the purpose of the treatment (prophylactic vs. therapeutic), the total weight of the patient treated, the route of administration, the ease of absorption, distribution, and excretion of the active agent by the body, the age and sensitivity of the patient to be treated, and the like, as will be apparent to a skilled artisan. The amount of administration can also be adjusted as the various factors change over time.

The active agents according to this invention (cells, nucleic acids, polypeptides and small organic compounds) can be administered to patients to be treated through any suitable routes of administration. Advantageously, the active agents are delivered to the patient parenterally, i.e., by intravenous, intramuscular, intraperiotneal, intracisternal, subcutaneous, or intraarticular injection or infusion.

For parenteral administration, the non-cell active agents can be formulated into solutions or suspensions, or in lyophilized forms for conversion into solutions or suspensions before use. Lyophilized compositions may include pharmaceutically acceptable carriers such as gelatin, DL-lactic and glycolic acids copolymer, D-mannitol, etc. To convert the lyophilized forms into solutions or suspensions, diluent containing, e.g., carboxymethylcellulose sodium, D-mannitol, polysorbate 80, glycerine, and water may be employed. Lyophilized forms may be stored in, e.g., a dual chamber syringe with one chamber containing the lyophilized composition and the other chamber containing the diluent. In addition, the active ingredient(s) can also be incorporated into sterile lyophilized microspheres for sustained release. Methods for making such microspheres are generally known in the art. See U.S. Pat. Nos. 4,652,441; 4,728,721; 4,849,228; 4,917,893; 4,954,298; 5,330,767; 5,476,663; 5,480,656; 5,575,987; 5,631,020; 5,631,021; 5,643,607; and 5,716,640.

In a solution or suspension form suitable for parenteral administration, the pharmaceutical composition can include, in addition to a therapeutically or prophylactically effective amount of an active agent of the present invention, a buffering agent, an isotonicity adjusting agent, a preservative, and/or an anti-absorbent. Examples of suitable buffering agent include, but are not limited to, citrate, phosphate, tartrate, succinate, adipate, maleate, lactate and acetate buffers, sodium bicarbonate, and sodium carbonate, or a mixture thereof. Preferably, the buffering agent adjusts the pH of the solution to within the range of 5-8. Examples of suitable isotonicity adjusting agents include sodium chloride, glycerol, mannitol, and sorbitol, or a mixture thereof. A preservative (e.g., antimicrobial agent) may be desirable as it can inhibit microbial contamination or growth in the liquid forms of the pharmaceutical composition. Useful preservatives may include benzyl alcohol, a paraben and phenol or a mixture thereof. Materials such as human serum albumin, gelatin or a mixture thereof may be used as anti-absorbents. In addition, conventional solvents, surfactants, stabilizers, pH balancing buffers, and antioxidants can all be used in the parenteral formulations, including but not limited to dextrose, fixed oils, glycerine, polyethylene glycol, propylene glycol, ascorbic acid, sodium bisulfite, and the like. The parenteral formulation can be stored in any conventional containers such as vials, ampoules, and syringes.

The active agents (particularly nucleic acids, polypeptides and small organic compounds) can also be delivered orally in enclosed gelatin capsules or compressed tablets. Capsules and tablets can be prepared in any conventional techniques. For example, the active agents can be incorporated into a formulation which includes pharmaceutically acceptable carriers such as excipients (e.g., starch, lactose), binders (e.g., gelatin, cellulose, gum tragacanth), disintegrating agents (e.g., alginate, Primogel, and corn starch), lubricants (e.g., magnesium stearate, silicon dioxide), and sweetening or flavoring agents (e.g., glucose, sucrose, saccharin, methyl salicylate, and peppermint). Various coatings can also be prepared for the capsules and tablets to modify the flavors, tastes, colors, and shapes of the capsules and tablets. In addition, liquid carriers such as fatty oil can also be included in capsules.

Other forms of oral formulations such as chewing gum, suspension, syrup, wafer, elixir, and the like can also be prepared containing the active compounds used in this invention. Various modifying agents for flavors, tastes, colors, and shapes of the special forms can also be included. In addition, for convenient administration by enteral feeding tube in patients unable to swallow, the active agents can be dissolved in an acceptable lipophilic vegetable oil vehicle such as olive oil, corn oil and safflower oil.

The active agents (e.g., nucleic acids in recombinant live vectors, polypeptides and small organic compounds) can also be administered topically through rectal, vaginal, nasal, bucal, or mucosal applications. Topical formulations are generally known in the art including creams, gels, ointments, lotions, powders, pastes, suspensions, sprays, drops and aerosols. Typically, topical formulations include one or more thickening agents, humectants, and/or emollients including but not limited to xanthan gum, petrolatum, beeswax, or polyethylene glycol, sorbitol, mineral oil, lanolin, squalene, and the like. A special form of topical administration is delivery by a transdermal patch. Methods for preparing transdermal patches are disclosed, e.g., in Brown, et al., *Annual Review of Medicine,* 39:221-229 (1988), which is incorporated herein by reference.

The active agents (e.g., cells, nucleic acids, polypeptides and small organic molecules) can also be delivered by subcutaneous implantation for sustained release. This may be accomplished by using aseptic techniques to surgically implant the active agents in any suitable formulation into the subcutaneous space of the anterior abdominal wall. See, e.g., Wilson et al., *J. Clin. Psych.* 45:242-247 (1984). Sustained release can be achieved by incorporating the active ingredients into a special carrier such as a hydrogel. Typically, a hydrogel is a network of high molecular weight biocompatible polymers, which can swell in water to form a gel like material. Hydrogels are generally known in the art. For example, hydrogels made of polyethylene glycols, or collagen, or poly(glycolic-co-L-lactic acid) are suitable for this invention. See, e.g., Phillips et al., *J. Pharmaceut. Sci.,* 73:1718-1720 (1984).

Alternatively, other forms controlled release or protection including microcapsules and nanocapsules generally known in the art, and hydrogels described above can all be utilized in oral, parenteral, topical, and subcutaneous administration of the active agents.

Another preferable delivery form is using liposomes as carrier. Liposomes are micelles formed from various lipids such as cholesterol, phospholipids, fatty acids, and derivatives thereof. Active compounds can be enclosed within such micelles. Methods for preparing liposomal suspensions containing active ingredients therein are generally known in the art and are disclosed in, e.g., U.S. Pat. No. 4,522,811, and Prescott, Ed., *Methods in Cell Biology,* Volume XIV, Academic Press, New York, N.Y. (1976), p. 33 et seq., both of which are incorporated herein by reference. Several anticancer drugs delivered in the form of liposomes are known in the art and are commercially available from Liposome Inc. of Princeton, N.J., U.S.A. It has been shown that liposomes can reduce the toxicity of the active agents, and increase their stability.

Example 1

Analysis of the PTAP (SEQ ID NO:1) Motif

Yeast two-hybrid assays were utilized to determine the effect of amino acid substitution mutations in the PTAP (SEQ ID NO:1) motif of HIV p6gag on the interaction between Tsg101 and p6gag. To prepare a yeast two-hybrid activation domain-Tsg101 construct, a DNA fragment encompassing the full-length coding sequence for Tsg101 according to GenBank Accession No. U82130 was obtained by PCR from a human fetal brain cDNA library and cloned into the EcoRI/Pst1 sites of the activation domain parent plasmid GADpN2 (LEU2, CEN4, ARS1, ADH1p-SV40NLS-GAL4 (768-881)-MCS (multiple cloning site)-PGKlt, AmpR, ColE1_ori).

To prepare the yeast two-hybrid DNA binding domain-HIV1 p6gag construct, a DNA fragment corresponding to the HIV1 p6 peptide derived from the HIV1.NL43 strain GAG protein was obtained by PCR from the NL43 containing plasmid R9Δapa and was cloned into the EcoRI/Sal1 sites of the binding domain parent plasmid pGBT.Q. The sequence of the amplified insert is shown in SEQ ID NO:34.

The following amino acid substitution mutations were introduced by PCR into the HIV1 p6gag sequence in the yeast two-hybrid binding domain-HIV1 p6gag construct described above. The mutations were verified by DNA sequence analysis. Such mutations are summarized in Table I below.

TABLE I

Tested Mutations in p6gag Protein

| Mutant Construct | p6gag Peptide Sequence Surrounding the PTAP (SEQ ID NO: 1) Motif | | | | | | | | | | | | |
|---|---|---|---|---|---|---|---|---|---|---|---|---|---|
| p6(wt) | S | R | P | E | P | T | A | P | P | E | E | S | F | R | F |
| p6(E6G) |   |   |   | G |   |   |   |   |   |   |   |   |   |   |   |
| p6(P7L) |   |   |   |   | L |   |   |   |   |   |   |   |   |   |   |
| p6(A9R) |   |   |   |   |   |   | R |   |   |   |   |   |   |   |   |
| p6(P10L) |   |   |   |   |   |   |   | L |   |   |   |   |   |   |   |

To test the effect of the mutations, yeast cells of the strain Y189 purchased from Clontech (ura3-52 his3*200 ade2-101 trp1-901 leu2-3,112 met gal4 gal80 URA3::GAL1p-lacZ) were co-transformed with the activation domain-Tsg101 construct and one of the binding domain-mutant p6gag constructs or the binding domain-wild type p6gag construct. Filter lift assays for β-Gal activity were conducted by lifting the transformed yeast colonies with filters, lysing the yeast cells by freezing and thawing, and contacting the lysed cells with X-Gal. Positive β-Gal activity indicates that the p6gag wild type or mutant protein interacts with Tsg101. All binding domain constructs were also tested for self-activation of β-Gal activity. The results are shown in Table II.

TABLE II

Interactions Between Tsg101 and p6gag

|  | p6(wt) | p6(E6G) | p6(P7L) | p6(A9R) | p6(P10L) |
|---|---|---|---|---|---|
| Tsg101 | + | + | − | − | − |
| p6(wt) | − | | | | |
| p6(E6G) | | − | | | |
| p6(P7L) | | | − | | |
| p6(A9R) | | | | − | |
| p6(P10L) | | | | | − |

Thus, as is clear from Table II, the mutations in the PTAP (SEQ ID NO:1) motif of HIV p6gag abolished the interaction between Tsg101 and HIV p6gag, while the p6/E6G mutation outside the PTAP (SEQ ID NO:1) motif did not result in the elimination of the Tsg101-p6gag interaction.

The interactions between TSG101 and wild-type p6gag (WT) or the p6gag PTAP (SEQ ID NO:1) mutants were further quantitated by performing liquid culture β-galactosidase assays. Cultures were grown overnight in synthetic media (−Leu, −Trp, +glucose) in 96 well plates, normalized for optical density, and lysed by addition of 6× lysis/substrate solution in 6× Z-buffer (60 mM KCl, 6 mM MgSO$_4$, 360 mM Na$_2$HPO$_4$, 240 mM NaH$_2$PO$_4$, 6 mg/ml CPRG, 0.12 U/ml lyticase, 0.075% NP-40). Cultures were incubated for 2 hr at 37° C., clarified by centrifugation, and the optical absorbance of each supernatant was measured (575 nm). Full length Tsg101 bound wild-type p6 in the two-hybrid liquid culture assay, resulting in high levels of β-galactosidase activity (>300-fold over background). Three different p6 point mutants were used to test whether the Tsg101 binding interaction required the PTAP (SEQ ID NO:1) late domain motif within HIV-1 p6, and all three (P6L, A9R and P10L) reduced β-galactosidase activity to background levels. Each of these point mutations also arrests HIV-1 budding at a late stage (Huang et al. 1995). These results are consistent with the hypothesis that the interaction between HIV p6gag and the human cellular protein TSG101 is essential for viral budding to occur.

Example 2

In Vitro Binding Assay

A fusion protein with a GST tag fused to the HIV-1 GAGp6 domain was recombinantly expressed and purified by chromatography. In addition, a GAGp6 peptide containing the first 14 amino acid residues ("p6(1-14)") was synthesized chemically by standard peptide synthesis methods. The peptide was purified by conventional protein purification techniques, e.g., by chromatography.

Nunc/Nalgene Maxisorp plates were incubated overnight at 4° C. or for 1-2 hrs at room temperature in 100 µl of a protein coupling solution containing purified GST-p6 and 50 mM Carbonate, pH=9.6. This allowed the attachment of the GST-p6 fusion protein to the plates. Liquids in the plates were then emptied and wells filled with 400 µl/well of a blocking buffer (SuperBlock; Pierce-Endogen, Rockford, Ill.). After incubating for 1 hour at room temperature, 100 µl of a mixture containing *Drosophila* S2 cell lysate myc-tagged Tsg101 (residues 1-207) and a specific amount of the p6(1-14) peptide were applied to the wells of the plate. This mixture was allowed to react for 2 hours at room temperature to form p6:Tsg101 protein-protein complexes.

Plates were then washed 4×100 µl with 1×PBST solution (Invitrogen; Carlsbad, Calif.). After washing, 100 µl of 1 µg/ml solution of anti-myc monoclonal antibody (Clone 9E10; Roche Molecular Biochemicals; Indianapolis, Ind.) in 1×PBST was added to the wells of the plate to detect the myc-epitope tag on the Tsg101 protein. Plates were then washed again with 4×100 µl with 1×PBST solution and 100 µl of 1 µg/ml solution of horseradish peroxidase (HRP) conjugated Goat anti-mouse IgG (Jackson Immunoresearch Labs; West Grove, Pa.) in 1×PBST was added to the wells of the plate to detect bound mouse anti-myc antibodies. Plates were then washed again with 4×100 µl with 1×PBST solution and 100 µl of fluorescent substrate (QuantaBlu; Pierce-Endogen, Rockford, Ill.) was added to all wells. After 30 minutes, 100 µl of stop solution was added to each well to inhibit the function of HRP. Plates were then read on a Packard Fusion instrument at an excitation wavelength of 325 nm and an emission wavelength of 420 nm. The presence of fluorescent signals indicates binding of Tsg101 to the fixed GST-p6. In contrast, the absence of fluorescent signals indicates that the PX$_1$X$_2$P-containing short peptide is capable of disrupting the interaction between Tsg101 and HIV p6.

Figure 3:
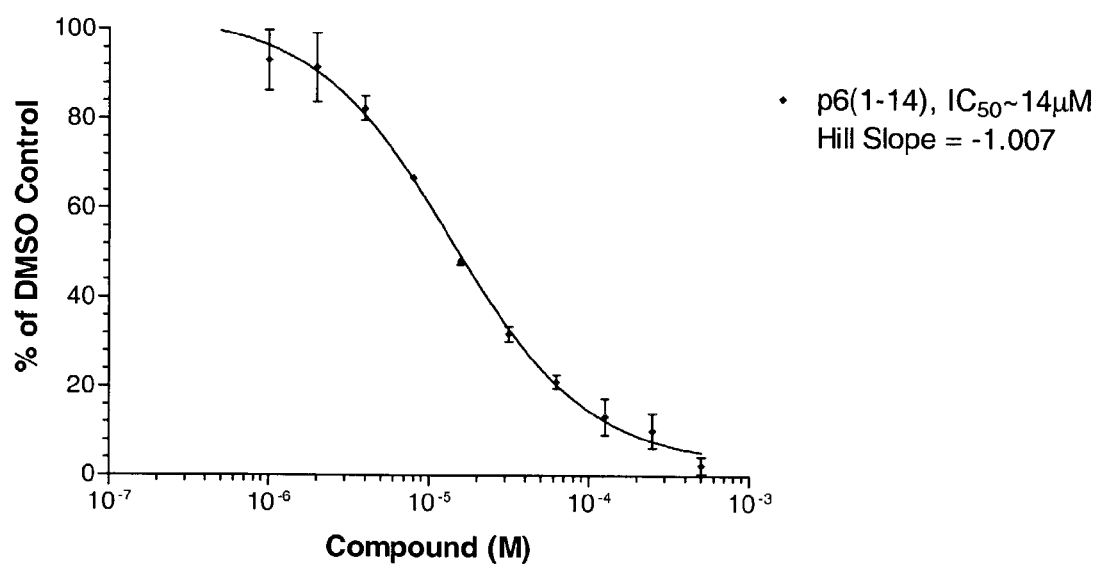
Figure 4:
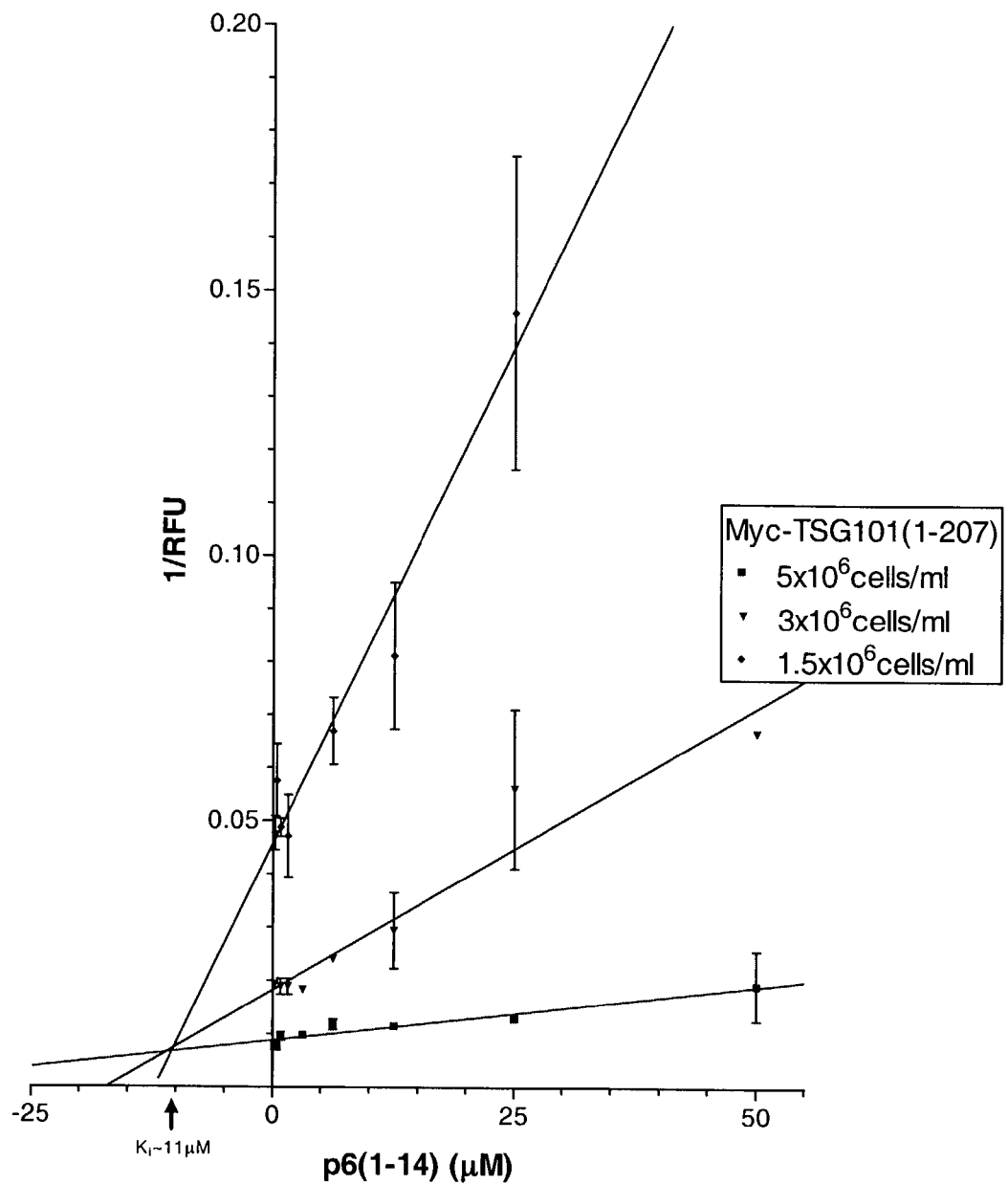
Figure 5:
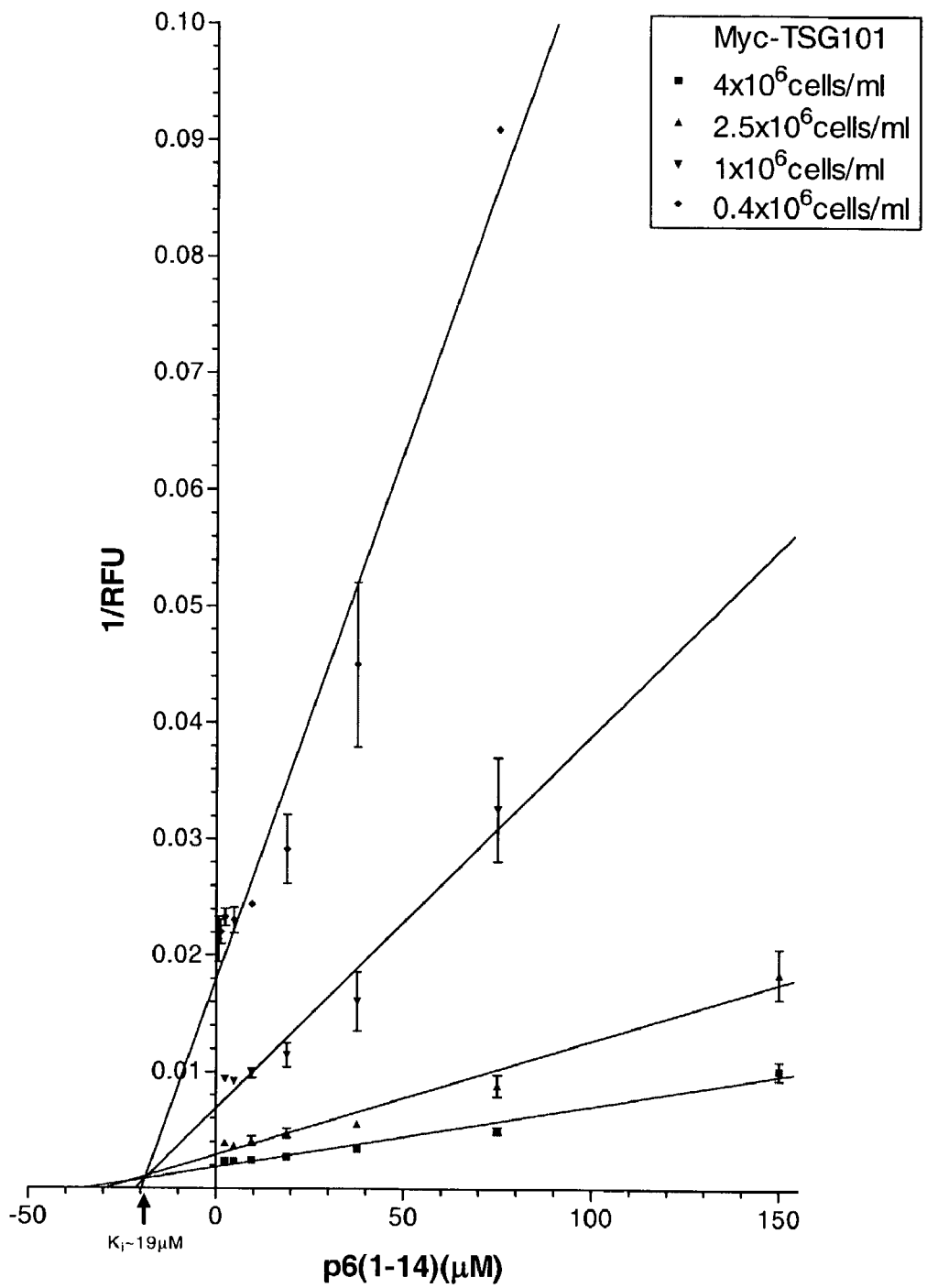

Different concentrations of the p6(1-14) peptide were tested, and the relative intensities of the fluorescence signals obtained at different concentrations were plotted against the peptide concentrations. The competitive inhibition curve is shown in FIG. 3. Two Dixon plots are shown in FIG. 4 and FIG. 5, respectively.

Example 3

Yeast Screen to Identify Small Molecule Inhibitors of the Interaction Between HIV GAGp6 and Tsg101

Beta-galactosidase is used as a reporter enzyme to signal the interaction between yeast two-hybrid protein pairs expressed from plasmids in *Saccharomyces cerevisiae*. Yeast strain MY209 (ade2 his3 leu2 trp1 cyh2 ura3::GAL1p-lacZ gal4 gal80 lys2::GAL1p-HIS3) bearing the plasmids Mp364 (LEU2 CEN4 ARS1 ADH1p-SV40NLS-GAL4 (768-881)-Tsg101 (1-390)-PGK1t AmpR ColE1_ori) and Mp206 (TRP1 CEN4 ARS ADH1p-GAL4(1-147)-HIV1_gag (448-500)-ADH1t AmpR ColE1_ori) is cultured in synthetic complete media lacking leucine and tryptophan (SC-Leu-Trp) overnight at 30° C. This culture is diluted to 0.01 OD$_{630}$ units/ml using SC-Leu-Trp media. The diluted MY209 culture is dispensed into 96-well microplates. Compounds from a library of small molecules are added to the microplates; the final concentration of test compounds is approximately 60 µM. The assay plates are incubated at 30° C. overnight.

The following day an aliquot of concentrated substrate/lysis buffer is added to each well and the plates incubated at 37° C. for 1-2 hours. At an appropriate time an aliquot of stop solution is added to each well to halt the beta-galactosidase reaction. For all microplates an absorbance reading is obtained to assay the generation of product from the enzyme substrate. The presence of putative inhibitors of the interaction between HIV p6 and Tsg101 results in inhibition of the beta-galactosidase signal generated by MY209. Additional testing eliminates compounds that decreased expression of beta-galactosidase by affecting yeast cell growth and non-specific inhibitors that affected the beta-galactosidase signal generated by the interaction of an unrelated protein pair.

Once a hit, i.e., a compound which inhibits the interaction between the viral and cellular proteins, is obtained, the compound is identified and subjected to further testing wherein the compounds are assayed at several concentrations to determine an $IC_{50}$ value, this being the concentration of the compound at which the signal seen in the two-hybrid assay described in this Example is 50% of the signal seen in the absence of the inhibitor.

Example 4

Efficacy of Peptidic Compounds

1. Materials

For antiviral tests, the following peptidic compounds (in Table III) were chemically synthesized and purified by conventional protein purification techniques:

TABLE III

| Compound | Formula | SEQ ID NO |
|---|---|---|
| MPI-PEP1 | $NH_2$—$(R)_9$-PEPTAPEE-COOH | 35 |
| MPI-PEP2 | $NH_2$—$(R)_9$-PEPTALEE-COOH | 36 |
| MPI-PEP3 | $NH_2$-RPEPTAP-CO—$NH_2$ | 37 |

The compounds were solubilized in sterile RPMI 1640 tissue culture medium to yield 40 mM stock solutions. AZT was used as a positive control antiviral compound.

Fresh human blood was obtained commercially from Interstate Blood Bank, Inc. (Memphis, Tenn.). The lymphotropic clinical isolate HIV-1$_{ROJO}$ was obtained from a pediatric patient attending the AIDS Clinic at the University of Alabama at Birmingham. The laboratory-adapted HIV-1$_{IIIB}$ strain was propagated and tittered in fresh human PBMCs; pre-titered aliquots of HIV-1$_{ROJO}$ and Hiv-1$_{IIIB}$ were removed from the freezer (−80° C.) and thawed rapidly to room temperature in a biological safety cabinet immediately before use. Phytohemagglutinin (PHA-P) was obtained from Sigma (St. Louis, Mo.) and recombinant IL-2 was obtained from Amgen (San Francisco, Calif.).

Anti-HIV Efficacy Evaluation in Fresh Human PBMCs

Fresh human PBMCs were isolated from screened donors, seronegative for HIV and HBV. Leukophoresed blood was diluted 1:1 with Dulbecco's phosphate buffered saline (PBS), layered over 14 mL of Ficoll-Hypaque density gradient in a 50 mL centrifuge tube and then centrifuged for 30 minutes at 600×g. Banded PBMCs were aspirated from the resulting interface and subsequently washed 2× with PBS by low speed centrifugation. After the final wash, cells were enumerated by trypan blue exclusion and re-suspended at $1×10^7$ cells/mL in RPMI 1640 supplemented with 15% Fetal Bovine Serum (FBS), 2 mM L-glutamine, 4 µg/mL PHA-P. The cells were allowed to incubate for 48-72 hours at 37° C. After incubation, PBMCs were centrifuged and reset in RPMI 1640 with 15% FBS, 2 mM L-glutamine, 100 U/ml penicillin, 100 µg/mL streptomycin, 10 µg/mL gentamycin, and 20 U/mL recombinant human IL-2. PBMCs were maintained in this medium at a concentration of $1-2×10^6$ cells/mL with biweekly medium changes until used in the assay protocol.

For the standard PBMC assay, PHA-P stimulated cells from at least two normal donors were pooled, diluted in fresh medium to a final concentration of $1×10^6$ cells/mL, and plated in the interior wells of 96 well round bottom microplate at 50 µL/well ($5×10^4$ cells/well). Test drug dilutions were prepared at a 2× concentration in microtiter tubes and 100 µL of each concentration was placed in appropriate wells in a standard format. 50 µL of a predetermined dilution of virus stock was placed in each test well (final MOI≈0.1). Wells with cells and virus alone were used for virus control. Separate plates were prepared identically without virus for drug cytotoxicity studies using an XTT assay system. The PBMC cultures were maintained for seven days following infection, at which time cell-free supernate samples were collected and assayed for reverse transcriptase activity as described below.

Reverse Transcriptase Activity Assay

A microtiter based reverse transcriptase (RT) reaction was utilized. See Buckheit et al., *AIDS Research and Human Retroviruses* 7:295-302 (1991). Tritiated thymidine triphosphate (NEN) (TTP) was resuspended in distilled $H_2O$ at 5 Ci/ml. Poly rA and oligo dT were prepared as a stock solution which was kept at −20° C. The RT reaction buffer was prepared fresh on a daily basis and consists of 125 µl 1M EGTA, 125 µl $dH_2O$, 110 µl 10% SDS, 50 µl 1M Tris (pH 7.4), 50 µl 1M DTT, and 40 µl 1M $MgCL_2$. These three solutions were mixed together in a ratio of 2 parts TTP, 1 part poly rA:oligo dT, and 1 part reaction buffer. Ten microliters of this reactions mixture was placed at a round bottom microtiter plate and 15 µl of virus containing supernatant was added and mixed. The plate was incubated at 37° C. in a water bath with a solid support to prevent submersion of the plate and incubated for 60 minutes. Following reaction, the reaction volume was spotted onto pieces of DE81 paper, washed 5 times 5 minutes each in a 5% sodium phosphate buffer, 2 times 1 minute each in distilled water, 2 times for 1 minute each in 70% ethanol, and then dried. Opti-Fluor-O (Packard) was added to each sample and incorporated radioactivity was quantified utilizing a Wallac 1450 MicroBeta Plus liquid scintillation counter.

Cytotoxicity Measurement By MTS Staining

At assay termination the assay plates were stained with the soluble tetrazolium-based dye MTS (CellTiter Reagent, Promega) to determine cell viability and quantify compound toxicity. MTS is metabolized by the mitochondria enzymes of metabolically active cells to yield a soluble formazan product, allowing the rapid quantitative analysis cell viability and compound cytotoxicity. The MTS is a stable solution that does not require preparation before use. At termination of the assay, 20 µl of MTS reagent was added per well. The wells were incubated overnight for the HIV cytoprotection assay at 37° C. The incubation intervals were chosen based on empirically determined times for optimal dye reduction in each cell type. Adhesive plate sealers were used in place of the lids, the sealed plate was inverted several times to mix the soluble formazan product and the plate was read spectrophotometrically at 490 nm with a Molecular Devices Vmax plate reader.

Data Analysis

Figure 6:
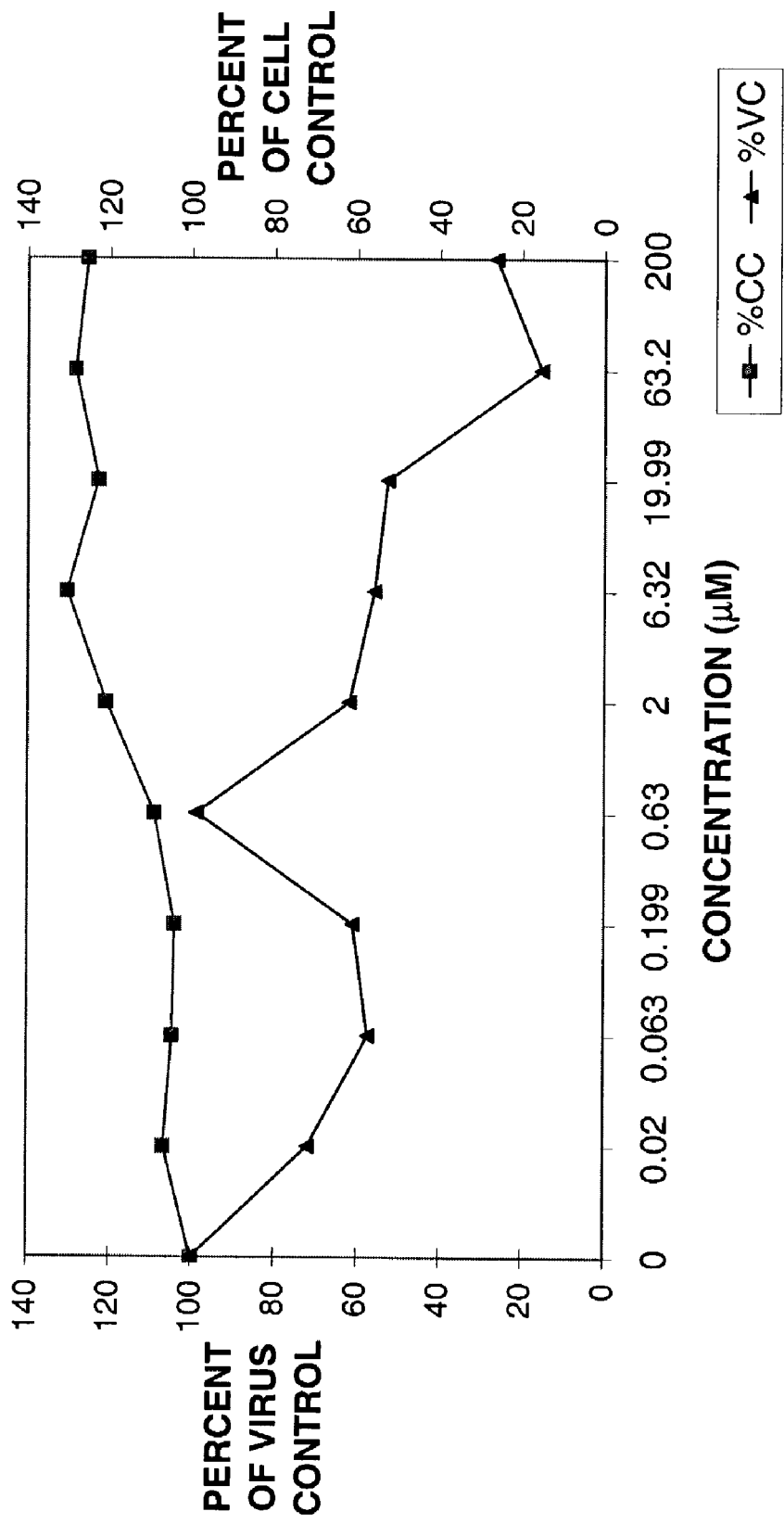
Figure 7:
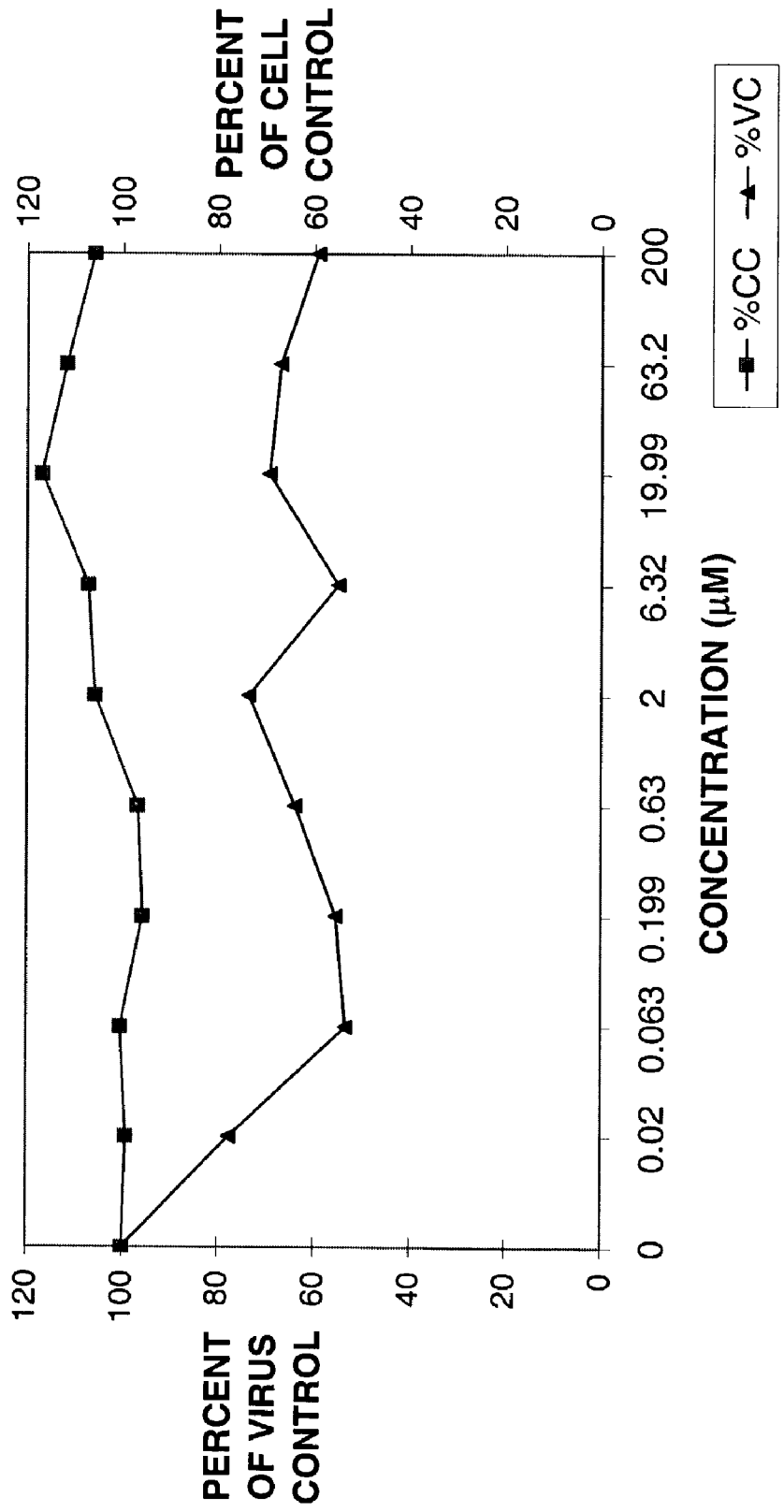
Figure 8:
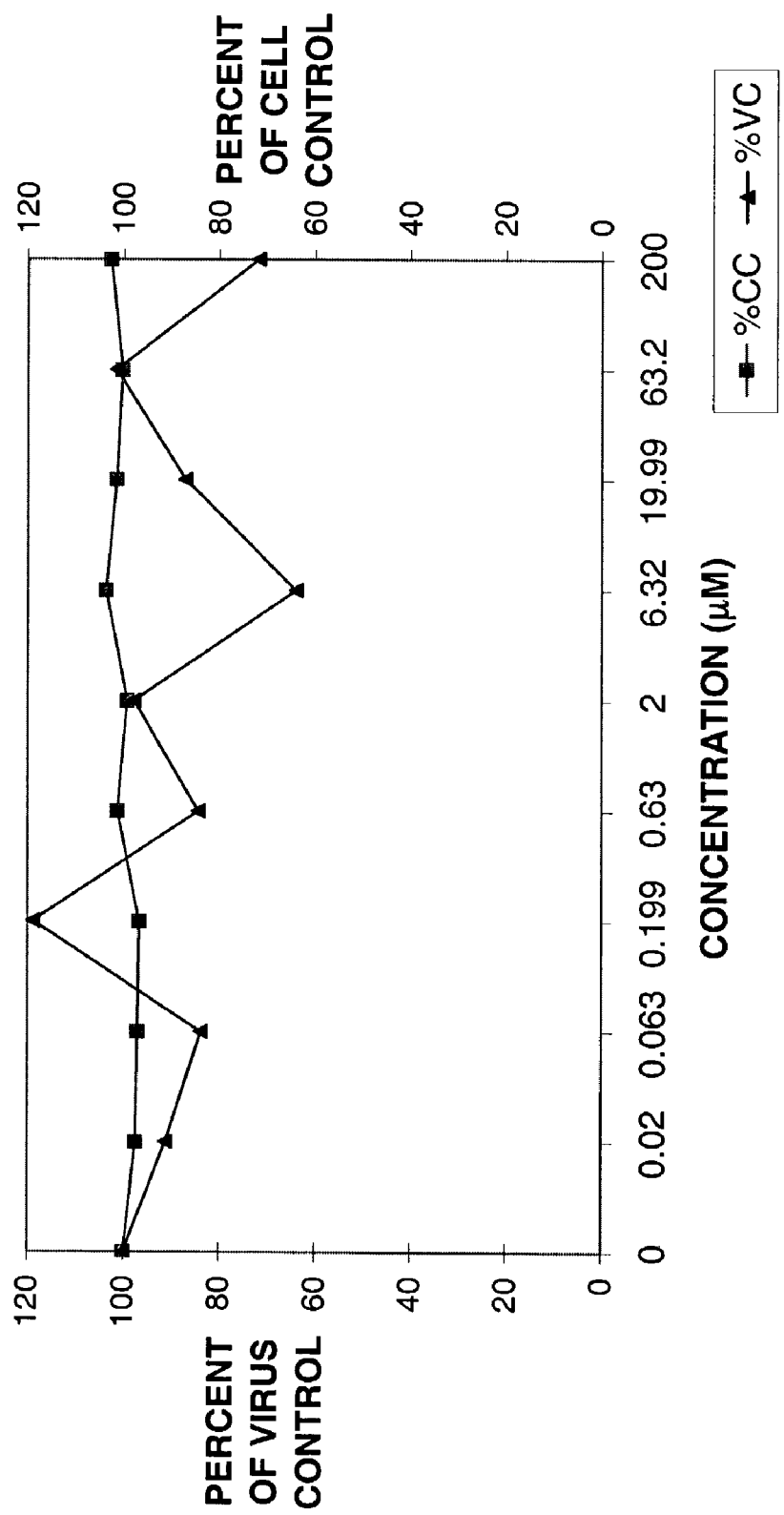
Figure 9:
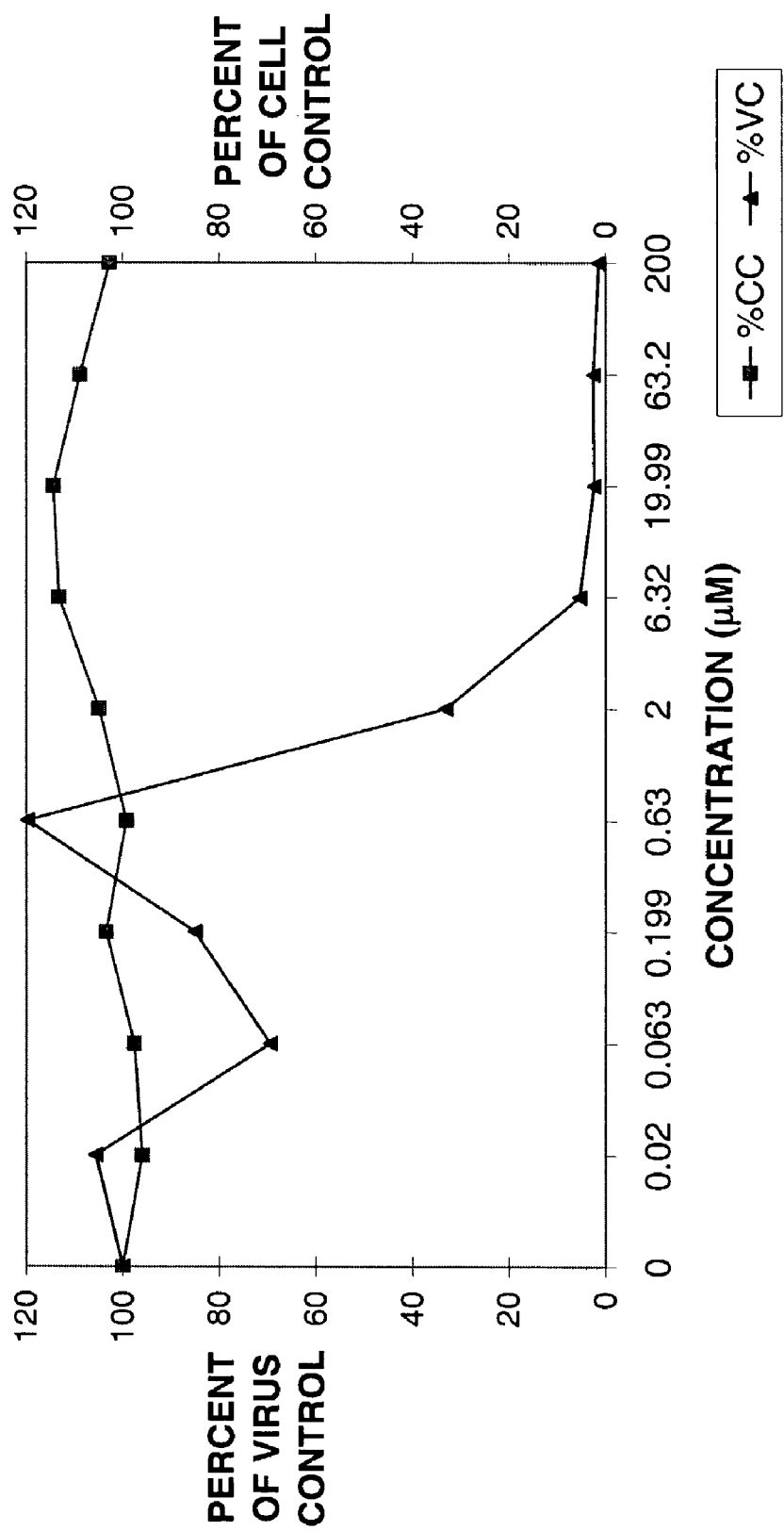

Indices including % CPE Reduction, % Cell Viability, $IC_{50}$, $TC_{50}$, and others were calculated and summarized in Table 4 below. The graphical results for the three peptidic compounds tested are displayed in FIGS. 6, 7 and 8, respectively. AZT was evaluated in parallel as a relevant positive control compound in the anti-HIV assay, and the graphical result is shown in FIG. 9.

TABLE IV

| Compound Name | IC$_{50}$ (μM) | TC$_{50}$ (μM) | Therapeutic Index | Comments |
|---|---|---|---|---|
| MPI-PEP1 | 21.7 | >200.0 | 9.2 | Active |
| MPI-PEP2 | >200.0 | >200.0 | N/A | Inactive |
| MPI-PEP3 | >200.0 | >200.0 | N/A | Inactive |
| AZT | 0.008 | >1.0 | >125.00 | Control; Highly Active |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

---

What is claimed is:

1. An immunizing composition comprising:
a mutant human immunodeficiency virus 1 (HIV1) proviral construct comprising a deletion or inactivation of the Tsg101 UEV binding domain (P(T/S)AP motif (SEQ ID NO:1 or SEQ ID NO:2) and a pharmaceutically acceptable adjuvant, wherein the expression of said construct in a host cell results in the assembly of HIV1 virus particles that are incapable of budding from the surface of said host cell, and remain attached to the surface of said host cell.

2. The composition of claim 1, wherein said adjuvant is capable of stimulating a cytotoxic T lymphocyte (CTL) response.

3. The composition of claim 2, wherein said adjuvant is a cytokine protein or a nucleic acid encoding a cytokine protein.

4. The composition of claim 3, wherein the cytokine protein is selected from the group consisting of IL-2, IL-4, IL-12, IL-18, gamma-interferon, and a fusion protein thereof.

5. The composition of claim 1, wherein said construct encodes a mutant HIV Pr55Gag polypeptide devoid of late domain motifs.

6. The composition of claim 5, wherein said construct is devoid of late domain motifs.

7. The composition of claim 5, wherein said construct further encodes another HIV protein or an immunogenic fragment thereof.

8. The composition of claim 7, wherein said HIV protein is a surface protein of HIV viral particles.

9. The composition of claim 8, wherein said HIV protein is an envelope protein.

10. The composition of claim 1, wherein said construct lacks the HIV Gag-p6 sequence.

11. The composition of claim 10, wherein the adjuvant is capable of stimulating a cytotoxic T lymphocyte (CTL) response.

12. The composition of claim 11, wherein said adjuvant is a cytokine protein or a nucleic acid encoding a cytokine protein.

13. The composition of claim 12, wherein said cytokine protein is selected from the group consisting of IL-2, IL-4, IL-12, IL-18, gamma-interferon, and a fusion protein thereof.

14. The composition of claim 12, wherein said adjuvant is (a) IL-2, (b) a fusion protein containing IL-2 and the Fc portion of immunoglobulin G (IgG), or (c) a nucleic acid encoding (a) or (b).

15. The composition of claim 10, wherein said construct further encodes another HIV protein or an immunogenic fragment thereof.

16. The composition of claim 15, wherein said HIV protein is a surface protein of HIV viral particles.

17. The composition of claim 16, wherein said HIV protein is an envelope protein.

18. An immunizing composition comprising:
a first nucleic acid encoding a mutant human immunodeficiency virus 1 (HIV1) sufficient for viral particle assembly but devoid of late domain motifs, wherein said mutant HIV1 comprises at least the membrane binding domain, major homology region, p2 domain, nucleocapsid domain, and the p1 domain of wild-type HIV1, and wherein expression of said first nucleic acid in a host cell results in the assembly of HIV1 virus particles that are incapable of budding from the surface of said host cell, and remain attached to the surface of said host cell; and
a second nucleic acid encoding a cytokine protein capable of stimulating a cytotoxic T lymphocyte (CTL) response.

19. The composition of claim 18, wherein said first nucleic acid is capable of directing the expression of a mutant HIV Pr55Gag polypeptide in the absence of HIV Rev protein.

20. The composition of claim 19, wherein said first nucleic acid has one or more mutations which decrease the effect of an inhibitory/instability sequence that is present in the corresponding nucleotide sequence of the native HIV GAG nucleic acid.

21. The composition of claim 18, wherein said cytokine protein is selected from the group consisting of IL-2, IL-4, IL-12, IL-18, gamma-interferon, and a fusion protein thereof.

22. The composition of claim 18, further comprising an adjuvant selected from IL-2 or a fusion protein containing IL-2 and the Fc portion of immunoglobulin G (IgG).

23. The composition of claim 18, further comprising a third nucleic acid encoding another HIV protein.

24. An expression vector comprising the first and second nucleic acids of claim 18.

25. The composition of claim 18, wherein said first nucleic acid encodes a mutant HIV1 having mutations in the P(T/S)AP sequence motif (SEQ ID NO:1 or SEQ ID NO:2) of the GAGp6 domain that abolish binding to Tsg101.

26. The composition of claim 18, wherein said first nucleic acid encodes a mutant HIV1 from which the P(T/S)AP sequence motif (SEQ ID NO:1 or SEQ ID NO:2) of the GAGp6 domain has been deleted.

27. The composition of claim 18, wherein said first nucleic acid encodes a mutant HIV 1 devoid of late domain motifs.

* * * * *

SEQUENCE LISTING

<160> NUMBER OF SEQ ID NOS: 37

<210> SEQ ID NO 1
<211> LENGTH: 4
<212> TYPE: PRT
<213> ORGANISM: Human immunodeficiency virus

<400> SEQUENCE: 1

Pro Thr Ala Pro
1

<210> SEQ ID NO 2
<211> LENGTH: 4
<212> TYPE: PRT
<213> ORGANISM: Human immunodeficiency virus

<400> SEQUENCE: 2

Pro Ser Ala Pro
1

<210> SEQ ID NO 3
<211> LENGTH: 4
<212> TYPE: PRT
<213> ORGANISM: Human immunodeficiency virus

<400> SEQUENCE: 3

Pro Ile Ala Pro
1

<210> SEQ ID NO 4
<211> LENGTH: 4
<212> TYPE: PRT
<213> ORGANISM: Human immunodeficiency virus

<400> SEQUENCE: 4

Pro Thr Thr Pro
1

<210> SEQ ID NO 5
<211> LENGTH: 4
<212> TYPE: PRT
<213> ORGANISM: Human immunodeficiency virus

<400> SEQUENCE: 5

Pro Ser Thr Pro
1

<210> SEQ ID NO 6
<211> LENGTH: 4
<212> TYPE: PRT
<213> ORGANISM: Human immunodeficiency virus

```
<400> SEQUENCE: 6

Pro Ile Thr Pro
1

<210> SEQ ID NO 7
<211> LENGTH: 5
<212> TYPE: PRT
<213> ORGANISM: Human immunodeficiency virus

<400> SEQUENCE: 7

Glu Pro Thr Ala Pro
1               5

<210> SEQ ID NO 8
<211> LENGTH: 5
<212> TYPE: PRT
<213> ORGANISM: Human immunodeficiency virus

<400> SEQUENCE: 8

Glu Pro Ser Ala Pro
1               5

<210> SEQ ID NO 9
<211> LENGTH: 5
<212> TYPE: PRT
<213> ORGANISM: Human immunodeficiency virus

<400> SEQUENCE: 9

Pro Thr Ala Pro Pro
1               5

<210> SEQ ID NO 10
<211> LENGTH: 5
<212> TYPE: PRT
<213> ORGANISM: Human immunodeficiency virus

<400> SEQUENCE: 10

Pro Ser Ala Pro Pro
1               5

<210> SEQ ID NO 11
<211> LENGTH: 6
<212> TYPE: PRT
<213> ORGANISM: Human immunodeficiency virus

<400> SEQUENCE: 11

Glu Pro Thr Ala Pro Pro
1               5

<210> SEQ ID NO 12
<211> LENGTH: 6
<212> TYPE: PRT
<213> ORGANISM: Human immunodeficiency virus

<400> SEQUENCE: 12

Glu Pro Ser Ala Pro Pro
1               5

<210> SEQ ID NO 13
<211> LENGTH: 6
<212> TYPE: PRT
<213> ORGANISM: Human immunodeficiency virus

<400> SEQUENCE: 13
```

```
Pro Glu Pro Thr Ala Pro
1               5

<210> SEQ ID NO 14
<211> LENGTH: 6
<212> TYPE: PRT
<213> ORGANISM: Human immunodeficiency virus

<400> SEQUENCE: 14

Pro Glu Pro Ser Ala Pro
1               5

<210> SEQ ID NO 15
<211> LENGTH: 7
<212> TYPE: PRT
<213> ORGANISM: Human immunodeficiency virus

<400> SEQUENCE: 15

Arg Pro Glu Pro Thr Ala Pro
1               5

<210> SEQ ID NO 16
<211> LENGTH: 7
<212> TYPE: PRT
<213> ORGANISM: Human immunodeficiency virus

<400> SEQUENCE: 16

Arg Pro Glu Pro Ser Ala Pro
1               5

<210> SEQ ID NO 17
<211> LENGTH: 7
<212> TYPE: PRT
<213> ORGANISM: Human immunodeficiency virus

<400> SEQUENCE: 17

Pro Glu Pro Thr Ala Pro Pro
1               5

<210> SEQ ID NO 18
<211> LENGTH: 7
<212> TYPE: PRT
<213> ORGANISM: Human immunodeficiency virus

<400> SEQUENCE: 18

Pro Glu Pro Ser Ala Pro Pro
1               5

<210> SEQ ID NO 19
<211> LENGTH: 8
<212> TYPE: PRT
<213> ORGANISM: Human immunodeficiency virus

<400> SEQUENCE: 19

Glu Pro Thr Ala Pro Pro Glu Glu
1               5

<210> SEQ ID NO 20
<211> LENGTH: 8
<212> TYPE: PRT
<213> ORGANISM: Human immunodeficiency virus

<400> SEQUENCE: 20

Glu Pro Ser Ala Pro Pro Glu Glu
1               5
```

```
<210> SEQ ID NO 21
<211> LENGTH: 8
<212> TYPE: PRT
<213> ORGANISM: Human immunodeficiency virus

<400> SEQUENCE: 21

Glu Pro Thr Ala Pro Pro Ala Glu
1               5

<210> SEQ ID NO 22
<211> LENGTH: 9
<212> TYPE: PRT
<213> ORGANISM: Human immunodeficiency virus

<400> SEQUENCE: 22

Pro Glu Pro Thr Ala Pro Pro Glu Glu
1               5

<210> SEQ ID NO 23
<211> LENGTH: 9
<212> TYPE: PRT
<213> ORGANISM: Human immunodeficiency virus

<400> SEQUENCE: 23

Pro Glu Pro Thr Ala Pro Pro Ala Glu
1               5

<210> SEQ ID NO 24
<211> LENGTH: 9
<212> TYPE: PRT
<213> ORGANISM: Human immunodeficiency virus

<400> SEQUENCE: 24

Pro Glu Pro Ser Ala Pro Pro Glu Glu
1               5

<210> SEQ ID NO 25
<211> LENGTH: 10
<212> TYPE: PRT
<213> ORGANISM: Human immunodeficiency virus

<400> SEQUENCE: 25

Arg Pro Glu Pro Thr Ala Pro Pro Glu Glu
1               5                   10

<210> SEQ ID NO 26
<211> LENGTH: 10
<212> TYPE: PRT
<213> ORGANISM: Human immunodeficiency virus

<400> SEQUENCE: 26

Arg Pro Glu Pro Ser Ala Pro Pro Glu Glu
1               5                   10

<210> SEQ ID NO 27
<211> LENGTH: 10
<212> TYPE: PRT
<213> ORGANISM: Human immunodeficiency virus

<400> SEQUENCE: 27

Arg Pro Glu Pro Thr Ala Pro Pro Ala Glu
1               5                   10

<210> SEQ ID NO 28
<211> LENGTH: 10
```

```
<212> TYPE: PRT
<213> ORGANISM: Human immunodeficiency virus

<400> SEQUENCE: 28

Arg Pro Glu Pro Ser Ala Pro Pro Ala Glu
1               5                   10

<210> SEQ ID NO 29
<211> LENGTH: 13
<212> TYPE: PRT
<213> ORGANISM: Human immunodeficiency virus

<400> SEQUENCE: 29

Leu Gln Ser Arg Pro Glu Pro Thr Ala Pro Pro Glu Glu
1               5                   10

<210> SEQ ID NO 30
<211> LENGTH: 13
<212> TYPE: PRT
<213> ORGANISM: Human immunodeficiency virus

<400> SEQUENCE: 30

Leu Gln Ser Arg Pro Glu Pro Ser Ala Pro Pro Glu Glu
1               5                   10

<210> SEQ ID NO 31
<211> LENGTH: 14
<212> TYPE: PRT
<213> ORGANISM: Human immunodeficiency virus

<400> SEQUENCE: 31

Leu Gln Ser Arg Pro Glu Pro Thr Ala Pro Pro Glu Glu Ser
1               5                   10

<210> SEQ ID NO 32
<211> LENGTH: 14
<212> TYPE: PRT
<213> ORGANISM: Human immunodeficiency virus

<400> SEQUENCE: 32

Leu Gln Ser Arg Pro Glu Pro Ser Ala Pro Pro Glu Glu Ser
1               5                   10

<210> SEQ ID NO 33
<211> LENGTH: 500
<212> TYPE: PRT
<213> ORGANISM: Human immunodeficiency virus

<400> SEQUENCE: 33

Met Gly Ala Arg Ala Ser Val Leu Ser Gly Gly Glu Leu Asp Lys Trp
1               5                   10                  15

Glu Lys Ile Arg Leu Arg Pro Gly Gly Lys Lys Gln Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Ile Ala Val Leu Tyr Cys Val His Gln Arg Ile Asp Val Lys Asp
                85                  90                  95

Thr Lys Glu Ala Leu Asp Lys Ile Glu Glu Glu Gln Asn Lys Ser Lys
            100                 105                 110
```

```
Lys Lys Ala Gln Gln Ala Ala Asp Thr Gly Asn Asn Ser Gln Val
    115                 120                 125

Ser Gln Asn Tyr Pro Ile Val Gln Asn Leu Gln Gly Gln Met Val His
130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Leu His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr His Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Pro Ala Thr Ile Met Ile Gln Lys Gly Asn Phe Arg
370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser His Lys Gly Arg Pro Gly Asn Phe
        435                 440                 445

Leu Gln Ser Arg Pro Glu Pro Thr Ala Pro Glu Glu Ser Phe Arg
450                 455                 460

Phe Gly Glu Glu Thr Thr Thr Pro Ser Gln Lys Gln Glu Pro Ile Asp
465                 470                 475                 480

Lys Glu Leu Tyr Pro Leu Ala Ser Leu Arg Ser Leu Phe Gly Ser Asp
                485                 490                 495

Pro Ser Ser Gln
            500

<210> SEQ ID NO 34
<211> LENGTH: 157
<212> TYPE: DNA
```

```
<213> ORGANISM: Human immunodeficiency virus

<400> SEQUENCE: 34
cttcagagca gaccagagcc aacagcccca ccagaagaga gcttcaggtt tggggaagag      60
acaacaactc cctctcagaa gcaggagccg atagacaagg aactgtatcc tttagcttcc     120
ctcagatcac tctttggcag cgaccccctcg tcacaat                              157

<210> SEQ ID NO 35
<211> LENGTH: 17
<212> TYPE: PRT
<213> ORGANISM: Artificial Sequence
<220> FEATURE:
<223> OTHER INFORMATION: Modified HIV peptide

<400> SEQUENCE: 35

Arg Arg Arg Arg Arg Arg Arg Arg Arg Pro Glu Pro Thr Ala Pro Glu
1               5                   10                  15

Glu

<210> SEQ ID NO 36
<211> LENGTH: 17
<212> TYPE: PRT
<213> ORGANISM: Artificial Sequence
<220> FEATURE:
<223> OTHER INFORMATION: Modified HIV peptide

<400> SEQUENCE: 36

Arg Arg Arg Arg Arg Arg Arg Arg Arg Pro Glu Pro Thr Ala Leu Glu
1               5                   10                  15

Glu

<210> SEQ ID NO 37
<211> LENGTH: 7
<212> TYPE: PRT
<213> ORGANISM: Artificial Sequence
<220> FEATURE:
<223> OTHER INFORMATION: Modified HIV peptide
<220> FEATURE:
<221> NAME/KEY: MOD_RES
<222> LOCATION: (7)..(7)
<223> OTHER INFORMATION: AMIDATION

<400> SEQUENCE: 37

Arg Pro Glu Pro Thr Ala Pro
1               5
```